(12) United States Patent
Dunkel et al.

(10) Patent No.: US 7,910,746 B2
(45) Date of Patent: *Mar. 22, 2011

(54) HALOALKYL CARBOXAMIDES

(75) Inventors: Ralf Dunkel, Lyons (FR); Hans-Ludwig Elbe, Langenfeld (DE); Benoit Hartmann, Langenfeld (DE); Jörg Nico Greul, Leichlingen (DE); Kerstin Ilg, Köln (DE); Ulrike Wachendorff-Neumann, Neuwied (DE); Peter Dahmen, Neuss (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 979 days.

This patent is subject to a terminal disclaimer.

(21) Appl. No.: 10/597,723

(22) PCT Filed: Jan. 22, 2005

(86) PCT No.: PCT/EP2005/000608
§ 371 (c)(1),
(2), (4) Date: May 16, 2007

(87) PCT Pub. No.: WO2005/075411
PCT Pub. Date: Aug. 18, 2005

(65) Prior Publication Data
US 2007/0203148 A1 Aug. 30, 2007

(30) Foreign Application Priority Data

Feb. 6, 2004 (DE) .......................... 10 2004 005 786

(51) Int. Cl.
*C07D 231/10* (2006.01)
*A01N 43/56* (2006.01)
(52) U.S. Cl. .................... 548/369.7; 514/406
(58) Field of Classification Search ............... 548/369.7; 514/406
See application file for complete search history.

(56) References Cited

U.S. PATENT DOCUMENTS

| | | | |
|---|---|---|---|
| 3,978,091 A | 8/1976 | Tsuchiya et al. | |
| 5,330,995 A | 7/1994 | Eicken et al. | |
| 5,438,070 A | 8/1995 | Eicken et al. | |
| 5,914,344 A * | 6/1999 | Yoshikawa et al. | 514/406 |
| 7,176,228 B2 | 2/2007 | Elbe et al. | |
| 7,208,169 B2 | 4/2007 | Dunkel et al. | |
| 7,314,958 B2 | 1/2008 | Elbe et al. | |
| 7,538,073 B2 | 5/2009 | Elbe et al. | |
| 7,598,389 B2 | 10/2009 | Dunkel et al. | |
| 7,687,531 B2 | 3/2010 | Dunkel et al. | |
| 2004/0204470 A1 | 10/2004 | Elbe et al. | |
| 2006/0128769 A1 | 6/2006 | Dunkel et al. | |
| 2007/0060579 A1 | 3/2007 | Wachendorff-Neumann et al. | |
| 2007/0082877 A1 | 4/2007 | Dunkel et al. | |
| 2007/0142327 A1 | 6/2007 | Funke et al. | |
| 2007/0203148 A1 | 8/2007 | Dunkel et al. | |
| 2007/0276022 A1 | 11/2007 | Dunkel et al. | |
| 2007/0293455 A1 | 12/2007 | Dunkel et al. | |
| 2008/0058389 A1 | 3/2008 | Dunkel et al. | |
| 2008/0064874 A1 | 3/2008 | Dunkel et al. | |
| 2008/0070863 A1 | 3/2008 | Funke et al. | |
| 2008/0085924 A1 | 4/2008 | Dunkel et al. | |
| 2008/0139389 A1 | 6/2008 | Kneen et al. | |
| 2008/0242708 A1 | 10/2008 | Dunkel et al. | |
| 2008/0261810 A1 | 10/2008 | Fischer et al. | |
| 2008/0293566 A1 | 11/2008 | Suty-Heinze et al. | |
| 2009/0036310 A1 | 2/2009 | Jakobi et al. | |
| 2009/0076113 A1 | 3/2009 | Dunkel et al. | |
| 2009/0105316 A1 | 4/2009 | Dunkel et al. | |
| 2009/0118346 A1 | 5/2009 | Dunkel et al. | |
| 2009/0209769 A1 | 8/2009 | Straub | |
| 2009/0270254 A1 | 10/2009 | Thielert et al. | |
| 2009/0286681 A1 | 11/2009 | Dahmen et al. | |
| 2009/0298888 A1 | 12/2009 | Thielert et al. | |
| 2010/0029730 A1 | 2/2010 | Dunkel et al. | |
| 2010/0056786 A1 | 3/2010 | Straub | |

FOREIGN PATENT DOCUMENTS

| | | |
|---|---|---|
| CA | 2 106 497 A1 | 3/1994 |
| DE | 2 006 472 A | 8/1970 |
| DE | 2 409 011 A | 9/1974 |
| EP | 0 545 099 A2 | 6/1993 |
| EP | 0 591 699 A1 | 4/1994 |
| EP | 0 824 099 B1 | 11/2001 |
| EP | 0 737 682 B1 | 1/2002 |
| EP | 0 589 301 B1 | 6/2002 |
| GB | 1 303 844 A1 | 1/1974 |

(Continued)

OTHER PUBLICATIONS

Office Action mailed on Feb. 3, 2009 for U.S. Appl. No. 10/588,293 inventors Dunkel, R., et al., filed May 16, 2007.
Office Action mailed on Aug. 12, 2009 for U.S. Appl. No. 10/588,293 inventors Dunkel, R., et al., filed May 16, 2007.
Co-pending U.S. Appl. No. 10/584,027 inventors Linker, Karl-Heinz et al., filed Dec. 18, 2004 (Not Published).
Co-pending U.S. Appl. No. 10/581,348 inventors Funke, Christian et al., filed Nov. 20, 2004 (Not Published).

(Continued)

*Primary Examiner* — Shailendra Kumar
(74) *Attorney, Agent, or Firm* — Sterne, Kessler, Goldstein & Fox P.L.L.C.

(57) ABSTRACT

New haloalkyl carboxamides of formula (I)

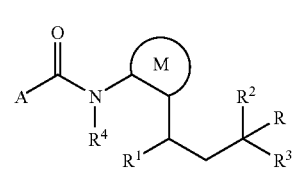

(I)

in which
R, $R^1$, $R^2$, $R^3$, $R^4$, M and A have the meanings specified in the description,
several processes for synthesizing these materials and their use in combating undesirable microorganisms, as well as new intermediate products and their synthesis.

6 Claims, No Drawings

FOREIGN PATENT DOCUMENTS

| | | |
|---|---|---|
| JP | 53-72823 A | 6/1978 |
| JP | 8-92223 A | 4/1996 |
| JP | 8-176112 A | 7/1996 |
| JP | 10-251240 A | 9/1998 |
| JP | 2001-72510 * | 3/2001 |
| JP | 2001-302605 A | 10/2001 |
| WO | WO 96/37494 A1 | 11/1996 |
| WO | WO 98/25923 A1 | 6/1998 |
| WO | WO 02/38542 A1 | 5/2002 |
| WO | WO 02/059086 A1 | 8/2002 |
| WO | WO 03/010149 A1 | 2/2003 |

OTHER PUBLICATIONS

Corey, E.J., "Studies on the Asymmetric Synthesis of α-Amino Acids. II. New System for Highly Specific Asymmetric Synthesis with Conservation of the Chiral Reagent," *J. Am. Chem. Soc.* 92:2488-2501, The American Chemical Society (1970).

Dialog File 351 Accession No. 297668, Derwent WPI English language abstract for DE 2 006 472 A (listed as document FP1 on accompanying form PTO/SB/08A).

Dialog File 351 Accession No. 660648, Derwent WPI English language abstract for DE 2 409 011 A (listed as document FP2 on accompanying form PTO/SB/08A).

Dialog File 351 Accession No. 1525166, Derwent WPI English language abstract for JP 53-72823 A (listed as document FP3 on accompanying form PTO/SB/08A).

Dialog File 351 Accession No. 6611019, Derwent WPI English language abstract for EP 0 545 099 A2 (listed as document FP4 on accompanying form PTO/SB/08A).

Dialog File 351 Accession No. 6720671, Derwent WPI English language abstract for EP 0 591 699 A1 (listed as document FP5 on accompanying form PTO/SB/08A).

Dialog File 351 Accession No. 7617971, Derwent WPI English language abstract for JP 8-92223 A (listed as document FP6 on accompanying form PTO/SB/08A).

Dialog File 351 Accession No. 7905153, Derwent WPI English language abstract for JP 8-176112 A (listed as document FP7 on accompanying form PTO/SB/08A).

Dialog File 351 Accession No. 9058768, Derwent WPI English language abstract for JP 10-251240 A (listed as document FP10 on accompanying form PTO/SB/08A).

Dialog File 351 Accession No. 11196304, Derwent WPI English language abstract for JP 2001302605 A (listed as document FP11 on accompanying form PTO/SB/08A).

Dialog File 351 Accession No. 6970179, Derwent WPI English language abstract for EP 0 589 301 A1 (listed as document FP15 on accompanying form PTO/SB/08A).

International Search Report for International Application No. PCT/EP2005/000608, European Patent Office, Netherlands, mailed on Jun. 20, 2005.

International Preliminary Report on Patentability for International Application No. PCT/EP2005/000608, European Patent Office, Netherlands, issued on Aug. 7, 2006.

Office Action mailed Dec. 8, 2008, in U.S. Appl. No. 10/557,083, Dunkel et al., filed May 27, 2006.

Office Action mailed May 12, 2009, in U.S. Appl. No. 10/557,083, Dunkel et al., filed May 27, 2006.

Office Action mailed Dec. 2, 2009, in U.S. Appl. No. 10/557,083, Dunkel et al., filed May 27, 2006.

Co-pending Application, U.S. Appl. No. 11/910,659, inventors Wachendorff-Neumann et al., filed on Oct. 4, 2007 (Not Published).

Co-pending Application, U.S. Appl. No. 12/654,384, inventors Fischer et al., filed on Dec. 17, 2009 (Not Published).

* cited by examiner

HALOALKYL CARBOXAMIDES

This application is a 371 of PCT/EP05/00608, filed Jan. 22, 2005.

The present invention pertains to new haloalkyl carboxamides, several processes for their synthesis and their use for combating undesired microorganisms.

It is already known that numerous carboxamides possess fungicidal properties (see, for example, WO 03/010149, WO 02/059086, EP-A 0 824 099, EP-A 0 737 682, EP-A 0 591 699, EP-A 0 589 301, EP-A 0 545 099, DE-A 24 09 011, DE-A 20 06 472, JP-A 2001-302605, JP-A 10-251240, JP-A 8-176112, JP-A 8-92223 and JP-A 53-72823). Thus numerous alkyl carboxamides have already become known that are not substituted in the alkyl portion, such as, for example, N-allyl-N-[2-(1,3-dimethylbutyl)phenyl]-1-methyl-3-(trifluoromethyl)-1H-pyrazole-4-carboxamide from WO 02/059086, N-[2-(1,3-dimethylbutyl)-phenyl]-2,4-dimethyl-1,3-thiazole-5-carboxamide from EP-A 0 824 099 and 5-fluoro-1,3-dimethyl-N-[2-(1,3,3-trimethylbutyl)phenyl]-1H-pyrazole-4-carboxamide from WO 03/010149. The effectiveness of these materials is good, but they leave something to be desired in many cases, for example at low application rates.

New haloalkyl carboxamides of the formula (I)

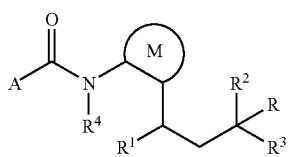

were found, in which
R stands for hydrogen or halogen,
$R^1$ stands for hydrogen or methyl,
$R^2$ stands for methyl, ethyl or $C_1$-$C_4$ haloalkyl with 1 to 9 fluorine, chlorine and/or bromine atoms,
$R^3$ stands for halogen or $C_1$-$C_4$ haloalkyl with 1 to 9 fluorine, chlorine and/or bromine atoms,
$R^4$ stands for hydrogen, $C_1$-$C_8$ alkyl, $C_1$-$C_6$ alkylsulfinyl, $C_1$-$C_6$ alkylsulfonyl, $C_1$-$C_4$-alkoxy-$C_1$-$C_4$-alkyl, $C_3$-$C_8$ cycloalkyl; $C_1$-$C_6$ haloalkyl, $C_1$-$C_4$ haloalkylthio, $C_1$-$C_4$ haloalkylsulfinyl, $C_1$-$C_4$ haloalkylsulfonyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$ alkyl) carbonyl-$C_1$-$C_3$-alkyl, halo-($C_1$-$C_3$ alkoxy)carbonyl-$C_1$-$C_3$-alkyl with 1 to 13 fluorine, chlorine and/or bromine atoms in each case;
($C_1$-$C_8$ alkyl)carbonyl, ($C_1$-$C_8$ alkoxy)carbonyl, ($C_1$-$C_4$-alkoxy-$C_1$-$C_4$-alkyl)carbonyl, ($C_3$-$C_8$ cycloalkyl)carbonyl; ($C_1$-$C_6$ haloalkyl)carbonyl, ($C_1$-$C_6$ haloalkoxy)carbonyl, (halo-$C_1$-$C_4$-alkoxy-$C_1$-$C_4$-alkyl)carbonyl, ($C_3$-$C_8$ halocycloalkyl)carbonyl with 1 to 9 fluorine, chlorine and/or bromine atoms in each case; or —C(=O)C(=O)$R^5$, —CONR$^{67}$ or —CH$_2$NR$^8$R$^9$,
$R^5$ stands for hydrogen, $C_1$-$C_8$ alkyl, $C_1$-$C_8$ alkoxy, $C_1$-$C_4$-alkoxy-$C_1$-$C_4$-alkyl, $C_3$-$C_8$ cycloalkyl; $C_1$-$C_6$ haloalkyl, $C_1$-$C_6$ haloalkoxy, halo-$C_1$-$C_4$-alkoxy$_1$-$C_4$-alkyl, $C_3$-$C_8$ halocycloalkyl with 1 to 9 fluorine, chlorine and/or bromine atoms in each case,
$R^6$ and $R^7$ stand independently of one another in each case for hydrogen, $C_1$-$C_8$ alkyl, $C_1$-$C_4$-alkoxy$_1$-$C_4$-alkyl, $C_3$-$C_8$ cycloalkyl; $C_1$-$C_8$ haloalkyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case,
$R^6$ and $R^7$, moreover, form a substituted, saturated heterocycle with 5 to 8 ring atoms together with the nitrogen atom to which they are bound, with single or multiple, the same or various substitution by halogen or $C_1$-$C_4$ alkyl, whereby the heterocycle can contain 1 or 2 additional, non-adjacent hetero atoms constituted by oxygen, sulfur or NR$^{10}$,
$R^8$ and $R^9$ stand independently of one another for hydrogen, $C_1$-$C_8$-alkyl, $C_3$-$C_8$ cycloalkyl; $C_1$-$C_8$ haloalkyl, $C_3$-$C_8$ halocycloalkyl with 1 to 9 fluorine, chlorine and/or bromine atoms in each case,
$R^8$ and $R^9$, moreover, form a substituted, saturated heterocycle with 5 to 8 ring atoms together with the nitrogen atom to which they are bound, with single or multiple, the same or various substitution by halogen or $C_1$-$C_4$ alkyl, whereby the heterocycle can contain 1 or 2 additional, non-adjacent hetero atoms constituted by oxygen, sulfur or NR$^{10}$,
$R^{10}$ stands for hydrogen or $C_1$-$C_6$ alkyl,
M stands in each case for a phenyl, pyridine or pyrimidine, pyridazine or pyrazine ring with a single substitution by $R^{11}$ or for a thiazole ring substituted by $R^{11\text{-}A}$,
$R^{11}$ stands for hydrogen, fluorine, chlorine, methyl, isopropyl, methylthio or trifluoromethyl,
$R^{11\text{-}A}$ stands for hydrogen, methyl, methylthio or trifluoromethyl,
A stands for the group of the formula (A1)

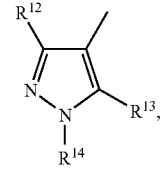

in which
$R^{12}$ stands for hydrogen, cyano, halogen, nitro, $C_1$-$C_4$ alkyl, $C_1$-$C_4$ alkoxy, $C_1$-$C_4$ alkylthio, $C_3$-$C_6$ cycloalkyl, $C_1$-$C_4$ haloalkyl, $C_1$-$C_4$ haloalkoxy or $C_1$-$C_4$ haloalkylthio, in each case with 1 to 5 halogen atoms, aminocarbonyl or aminocarbonyl-$C_1$-$C_4$-alkyl,
$R^{13}$ stands for hydrogen, halogen, cyano, $C_1$-$C_4$ alkyl, $C_1$-$C_4$ alkoxy or $C_1$-$C_4$ alkylthio,
$R^{14}$ stands for hydrogen, $C_1$-$C_4$ alkyl, hydroxy-$C_1$-$C_4$ alkyl, $C_2$-$C_6$ alkenyl, $C_3$-$C_6$ cycloalkyl, $C_1$-$C_4$-alkylthio-$C_1$-$C_4$-alkyl, $C_1$-$C_4$-alkoxy-$C_1$-$C_4$-alkyl, $C_1$-$C_4$ haloalkyl, $C_1$-$C_4$-haloalkylthio-$C_1$-$C_4$-alkyl, $C_1$-$C_4$-haloalkoxy-$C_1$-$C_4$-alkyl in each case with 1 to 5 halogen atoms, or phenyl,
or
A stands for the group of the formula (A2)

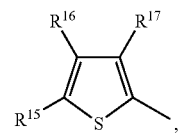

in which
$R^{15}$ and $R^{16}$ stand independently of one another for hydrogen, halogen, $C_1$-$C_4$ alkyl or $C_1$-$C_4$ haloalkyl with 1 to 5 halogen atoms, $R^{17}$ stands for halogen, cyano or $C_1$-$C_4$ alkyl, or $C_1$-$C_4$ haloalkyl or $C_1$-$C_4$ haloalkoxy with 1 to 5 halogen atoms in each case, or A stands for the group of the formula (A3)

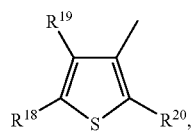

(A3)

in which
$R^{18}$ and $R^{19}$ stand independently of one another for hydrogen, halogen, $C_1$-$C_4$ alkyl or $C_1$-$C_4$ haloalkyl with 1 to 5 halogen atoms,
$R^{20}$ stands for hydrogen, halogen, $C_1$-$C_4$ alkyl or $C_1$-$C_4$ haloalkyl with 1 to 5 halogen atoms, or A stands for the group of the formula (A4)

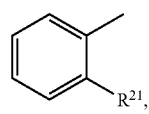

(A4)

in which
$R^{21}$ stands or hydrogen, halogen, hydroxy, cyano, $C_1$-$C_6$ alkyl, $C_1$-$C_4$ haloalkyl, $C_1$-$C_4$ haloalkoxy or $C_1$-$C_4$ haloalkylthio in each case with 1 to 5 halogen atoms, or A stands for the group of the formula (A5)

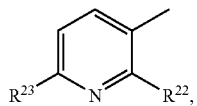

(A5)

in which
$R^{22}$ stands for halogen, hydroxy, cyano, $C_1$-$C_4$ alkyl, $C_1$-$C_4$ alkoxy, $C_1$-$C_4$ alkylthio, $C_1$-$C_4$ haloalkyl, $C_1$-$C_4$ haloalkylthio or $C_1$-$C_4$ haloalkoxy in each case with 1 to 5 halogen atoms,
$R^{23}$ stands for hydrogen, halogen, cyano, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy in each case with 1 to 5 halogen atoms, $C_1$-$C_4$ alkylsulfinyl or $C_1$-$C_4$ alkylsulfonyl, or A stands for the group of the formula (A6)

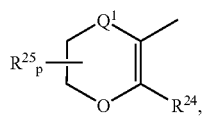

(A6)

in which
$R^{24}$ stands for $C_1$-$C_4$ alkyl or $C_1$-$C_4$ haloalkyl with 1 to 5 halogen atoms, $R^{25}$ stands for $C_1$-$C_4$ alkyl,
$Q^1$ stands for S (sulfur), O (oxygen), SO, $SO_2$ or $CH_2$,
p stands for 0, 1 or 2, whereby $R^{25}$ stands for identical or various groups if p is 2, or A stands for the group of the formula (A7)

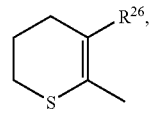

(A7)

in which
$R^{26}$ stands for $C_1$-$C_4$ alkyl or $C_1$-$C_4$ haloalkyl with 1 to 5 halogen atoms, or A stands for the group of the formula (A8)

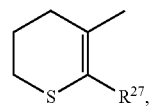

(A8)

in which
$R^{27}$ stands for $C_1$-$C_4$ alkyl or $C_1$-$C_4$ haloalkyl with 1 to 5 halogen atoms, or A stands for the group of the formula (A9)

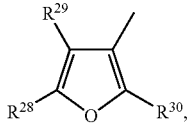

(A9)

in which
$R^{28}$ and $R^{29}$ stand independently of one another for hydrogen, halogen, amino, $C_1$-$C_4$ alkyl or $C_1$-$C_4$ haloalkyl with 1 to 5 halogen atoms,
$R^{30}$ stands for hydrogen, halogen, $C_1$-$C_4$ alkyl or $C_1$-$C_4$ haloalkyl with 1 to 5 halogen atoms, or A stands for the group of the formula (A10)

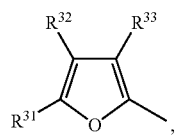

(A10)

in which
$R^{31}$ and $R^{32}$ stand independently of one another for hydrogen, halogen, amino, nitro, $C_1$-$C_4$ alkyl or $C_1$-$C_4$ haloalkyl with 1 to 5 halogen atoms,
$R^{33}$ stands for hydrogen, halogen, $C_1$-$C_4$ alkyl or $C_1$-$C_4$ haloalkyl with 1 to 5 halogen atoms, or A stands for the group of the formula (A11)

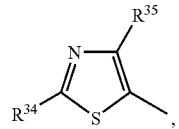
(A11)

in which
R³⁴ stands for hydrogen, halogen, amino, $C_1$-$C_4$ alkylamino, di-($C_1$-$C_4$ alkyl)amino, cyano, $C_1$-$C_4$ alkyl or $C_1$-$C_4$ haloalkyl with 1 to 5 halogen atoms,
R³⁵ stands for halogen, $C_1$-$C_4$ alkyl or $C_1$-$C_4$ haloalkyl with 1 to 5 halogen atoms, or A stands for the group of the formula (A12)

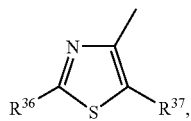
(A12)

in which
R³⁶ stands for hydrogen, halogen, amino, $C_1$-$C_4$ alkylamino, di-($C_1$-$C_4$ alkyl)amino, cyano, $C_1$-$C_4$ alkyl or $C_1$-$C_4$ haloalkyl with 1 to 5 halogen atoms,
R³⁷ stands for halogen, $C_1$-$C_4$ alkyl or $C_1$-$C_4$ haloalkyl with 1 to 5 halogen atoms, or A stands for the group of the formula (A13)

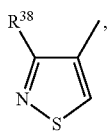
(A13)

in which
R³⁸ stands for halogen, $C_1$-$C_4$ alkyl or $C_1$-$C_4$ haloalkyl with 1 to 5 halogen atoms, or A stands for the group of the formula (A14)

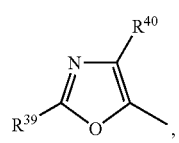
(A14)

in which
R³⁹ stands for hydrogen or $C_1$-$C_4$ alkyl,
R⁴⁰ stands for halogen or $C_1$-$C_4$ alkyl, or A stands for the group of the formula (A15)

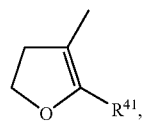
(A15)

in which
R⁴¹ stands for $C_1$-$C_4$ alkyl or $C_1$-$C_4$ haloalkyl with 1 to 5 halogen atoms, or A stands for the group of the formula (A16)

(A16)

in which
R⁴² stands for hydrogen, halogen, $C_1$-$C_4$ alkyl or $C_1$-$C_4$ haloalkyl with 1 to 5 halogen atoms, or A stands for the group of the formula (A17)

(A17)

in which
R⁴³ stands for halogen, hydroxy, $C_1$-$C_4$ alkyl, $C_1$-$C_4$ alkoxy, $C_1$-$C_4$ alkylthio, $C_1$-$C_4$ haloalkyl, $C_1$-$C_4$ haloalkylthio or $C_1$-$C_4$ haloalkoxy with 1 to 5 halogen atoms in each case, or A stands for the group of the formula (A18)

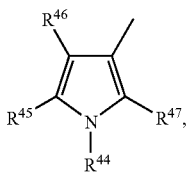
(A18)

in which
R⁴⁴ stands for hydrogen, cyano, $C_1$-$C_4$ alkyl, $C_1$-$C_4$ haloalkyl with 1 to 5 halogen atoms, $C_1$-$C_4$-alkoxy-$C_1$-$C_4$ alkyl, hydroxy-$C_1$-$C_4$ alkyl, $C_1$-$C_4$ alkylsulfonyl, di($C_1$-$C_4$ alkyl)aminosulfonyl, $C_1$-$C_6$ alkylcarbonyl or in each case possibly substituted phenylsulfonyl or benzoyl,
R⁴⁵ stands for hydrogen, halogen, $C_1$-$C_4$ alkyl or $C_1$-$C_4$ haloalkyl with 1 to 5 halogen atoms,
R⁴⁶ stands for hydrogen, halogen, cyano, $C_1$-$C_4$ alkyl or $C_1$-$C_4$ haloalkyl with 1 to 5 halogen atoms,
R⁴⁷ stands for hydrogen, halogen, $C_1$-$C_4$ alkyl or $C_1$-$C_4$ haloalkyl with 1 to 5 halogen atoms, or
A stands for the group of the formula (A19)

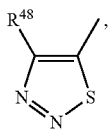

(A19)

in which
R$^{48}$ stands for C$_1$-C$_4$ alkyl.

Furthermore, it was found that haloalkyl carboxamides of the formula (I) are obtained by reacting Furthermore, it was found that hexylcarboxanilides of the formula (I) are obtained by reacting a) carboxylic acid derivatives the formula (II)

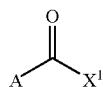

(II)

in which
A has the meanings specified above and
X$^1$ stands for halogen or hydroxy,
with aniline derivatives of the formula (III)

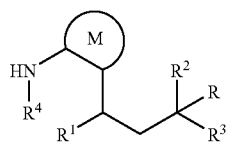

(III)

in which R, R$^1$, R$^2$, R$^3$, R$^4$ and M have the meanings specified above,
possibly in the presence of a catalyst, possibly in the presence a condensation agent,
possibly in the presence of an acid binder and possibly in the presence of a diluent,
or
b) Hexylcarboxanilides of the formula (I-a)

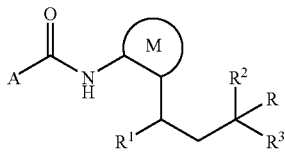

(I-a)

in which R, R$^1$, R$^2$, R$^3$, M and A have the meanings specified above
with halides of the formula (IV)

R$^{4-4}$—X$^2$ (IV)

in which
X$^2$ stands for chlorine, bromine or iodine,
R$^{4-4}$ stands for C$_1$-C$_8$ alkyl, C$_1$-C$_6$ alkylsulfinyl, C$_1$-C$_6$ alkylsulfonyl, C$_1$-C$_4$-alkoxy-C$_1$-C$_4$-alkyl, C$_3$-C$_8$ cycloalkyl; C$_1$-C$_6$ haloalkyl, C$_1$-C$_4$ haloalkylthio, C$_1$-C$_4$ haloalkylsulfinyl, C$_1$-C$_4$ haloalkylsulfonyl, halo-C$_1$-C$_4$-alkoxy-C$_1$-C$_4$-alkyl, C$_3$-C$_8$ halocycloalkyl with 1 to 9 fluorine, chlorine and/or bromine atoms in each case; formyl, formyl-C$_1$-C$_3$-alkyl, (C$_1$-C$_3$-alkyl)carbonyl-C$_1$-C$_3$-alkyl, (C$_1$-C$_3$-alkoxy)carbonyl-C$_1$-C$_3$-alkyl; halo-(C$_1$-C$_3$ alkyl)carbonyl-C$_1$-C$_3$-alkyl, halo-(C$_1$-C$_3$ alkoxy)carbonyl-C$_1$-C$_3$-alkyl with 1 to 13 fluorine, chlorine and/or bromine atoms in each case;

(C$_1$-C$_8$ alkyl)carbonyl, (C$_1$-C$_8$ alkoxy)carbonyl, (C$_1$-C$_4$-alkoxy-C$_1$-C$_4$-alkyl)carbonyl, (C$_3$-C$_8$ cycloalkyl)carbonyl; (C$_1$-C$_6$ haloalkyl)carbonyl, (C$_1$-C$_6$ haloalkoxy)carbonyl, (halo-C$_1$-C$_4$-alkoxy-C$_1$-C$_4$-alkyl)carbonyl, (C$_3$-C$_8$ halocycloalkyl)carbonyl with 1 to 9 fluorine, chlorine and/or bromine atoms in each case; or —C(=O)C(=O)R$^5$, —CONR$^6$R$^7$ or —CH$_2$NR$^8$R$^9$, whereby R$^5$, R$^6$, R$^7$, R$^8$ and R$^9$ have the meanings specified above, in the presence of a base and in the presence of a dilution medium.

Lastly, it was found that the new haloalkyl carboxamides of the formula (I) have very good microbicidal properties and can be used for combating undesirable microorganisms for both crop protection and material protection.

The inventive compounds may be present as mixtures of various possible to isomeric forms, particularly of stereoisomers, such as, for example, E- and Z-, threo- and erythro-, as well as optical isomers, but also as a where applicable. The E- and Z-isomers, the threo-, erythro-, and optical isomers and any mixtures of these isomers as well as possible tautomeric forms are claimed.

The inventive haloalkyl carboxamides are defined in general by the formula (I). Preferred group definitions of the formulas given previously and hereafter are specified below. These definitions apply equally to the end products of the formula (I) as well as to all intermediate products.

R stands preferably for hydrogen, fluorine, chlorine or bromine.

R stands particularly preferably for hydrogen.

R furthermore stands particularly preferably for fluorine or chlorine.

R$^1$ stands preferably for hydrogen.

R$^1$ furthermore stands preferably for methyl.

R$^2$ stands preferably for methyl, ethyl or in each case methyl, ethyl, n- or isopropyl, n-, iso-, sec- or tert-butyl, singly or multiply, the same or variously substituted by fluorine, chlorine or bromine.

R$^2$ stands particularly preferably for methyl, ethyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2,2-dichloro-2-fluoroethyl, 2,2,2-trichloroethyl, 1-chlorobutyl, heptafluoro-n-propyl or heptafluoroisopropyl.

R$^2$ stands most particularly preferably for methyl, ethyl or trifluoromethyl.

R$^2$ stands a for methyl.

R$^2$ furthermore stands especially preferably for ethyl.

R$^2$ furthermore stands especially preferably for trifluoromethyl.

R$^3$ stands preferably for fluorine, chlorine, bromine, iodine or in each case methyl, ethyl, n- or isopropyl, n-, iso-, sec- or tert-butyl, singly or multiply, the same or variously substituted by fluorine, chlorine or bromine.

R$^3$ stands particularly preferably for fluorine, chlorine, bromine, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2,2-dichloro-2-fluoroethyl, 2,2,2-trichloroethyl, 1-chlorobutyl, heptafluoro-n-propyl or heptafluoroisopropyl.

$R^3$ stands most particularly preferably for chlorine or trifluoromethyl.

$R^3$ stands especially preferably for chlorine.

$R^3$ furthermore stands especially preferably for trifluoromethyl.

$R^4$ stands preferably for hydrogen, $C_1$-$C_6$ alkyl, $C_1$-$C_4$ alkylsulfinyl, $C_1$-$C_4$ alkylsulfonyl, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkylthio, $C_1$-$C_4$ haloalkylsulfinyl, $C_1$-$C_4$ haloalkylsulfonyl, halo-$C_1$-$C_3$-alkoxy-$C_1$-$C_3$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$ alkyl)carbonyl-$C_1$-$C_3$-alkyl, halo-($C_1$-$C_3$ alkoxy)carbonyl-$C_1$-$C_3$-alkyl with 1 to 13 fluorine, chlorine and/or bromine atoms in each case;

($C_1$-$C_6$ alkyl)carbonyl, ($C_1$-$C_4$ alkoxy)carbonyl, ($C_1$-$C_3$-alkoxy-$C_1$-$C_3$-alkyl)carbonyl, ($C_3$-$C_6$ cycloalkyl)carbonyl; ($C_1$-$C_4$ haloalkoxy)carbonyl, ($C_1$-$C_4$ haloalkoxy)carbonyl, (halo-$C_1$-$C_3$-alkoxy-$C_1$-$C_3$-alkyl)carbonyl, ($C_3$-$C_6$ halocycloalkyl)carbonyl with 1 to 9 fluorine, chlorine and/or bromine atoms in each case; or —C(=O)C(=O)$R^5$, —CONR$^6$R$^7$ or —CH$_2$NR$^3$R$^9$.

$R^4$ stands particularly preferably for hydrogen, methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulfinyl, trifluoromethylsulfonyl, trifluoromethoxymethyl; formyl, —CH$_2$—CHO, —(CH$_2$)$_2$ —CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethyl carbonyl, trifluoromethoxycarbonyl, or —C(=O)C(=O)$R^5$, —CONR$^{67}$ or —CH$_2$NR$^8$R$^9$.

$R^4$ stands most particularly preferably for hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$R^5$ stands preferably for hydrogen, $C_1$-$C_6$ alkyl, $C_1$-$C_4$ alkoxy, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkoxy, halo-$C_1$-$C_3$-alkoxy-$C_1$-$C_3$-alkyl, $C_3$-$C_6$ halocycloalkyl with 1 to 9 fluorine, chlorine and/or bromine atoms in each case.

$R^5$ stands particularly preferably for hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^6$ and $R^7$ stand independently of one another preferably for hydrogen, $C_1$-$C_6$ alkyl, $C_1$-$C_3$-alkoxy-$C_1$-$C_3$-alkyl, $C_3$-$C_6$ cycloalkyl; $C_1$-$C_4$ haloalkyl, halo-$C_1$-$C_3$-alkoxy-$C_1$-$C_3$-alkyl, $C_3$-$C_6$ halocycloalkyl with 1 to 9 fluorine, chlorine and/or bromine atoms in each case.

$R^6$ and $R^7$, moreover, form a saturated, substituted heterocycle together with the nitrogen atom to which they are bound, preferably one with 5 or 6 ring atoms and single to quadruple, the same or various substitution by halogen or $C_1$-$C_4$ alkyl, whereby the heterocycle can contain 1 or 2 additional, non-adjacent hetero atoms constituted by oxygen, sulfur or NR$^{10}$.

$R^6$ and $R^7$ stand independently of one another particularly preferably for hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^6$ and $R^7$, moreover, particularly preferably form a substituted unsaturated heterocycle with the nitrogen atom to which they are bound, preferably one singly to quadruply substituted by the same or various substitutents comprised of fluorine, chlorine, bromine or methyl, said heterocycle being a morpholine, thiomorpholine or piperazine, whereby the piperazine can be substituted by $R^{10}$ at the second nitrogen atom.

$R^8$ and $R^9$ stand independently of one another preferably for hydrogen, $C_1$-$C_6$ alkyl, $C_3$-$C_6$ cyclo-alkyl; $C_1$-$C_4$ haloalkyl, $C_3$-$C_6$ halocycloalkyl with 1 to 9 fluorine, chlorine and/or bromine atoms in each case.

$R^8$ and $R^9$, moreover, form a saturated, substituted heterocycle together with the nitrogen atom to which they are bound, preferably one with 5 or 6 ring atoms and single to quadruple, the same or various substitution by halogen or $C_1$-$C_4$ alkyl, whereby the heterocycle can contain 1 or 2 additional, non-adjacent hetero atoms constituted by oxygen, sulfur or NR$^{10}$.

$R^8$ and $R^9$ stand independently of one another particularly preferably for hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^8$ and $R^9$, moreover, particularly preferably form a substituted unsaturated heterocycle with the nitrogen atom to which they are bound, preferably one singly to quadruply substituted by the same or various substitutents comprised of fluorine, chlorine, bromine or methyl, said heterocycle being a morpholine, thiomorpholine or piperazine, whereby the piperazine can be substituted by $R^{10}$ at the second nitrogen atom.

$R^{10}$ stands preferably for hydrogen or $C_1$-$C_4$ alkyl.

$R^{10}$ stands particularly preferably for hydrogen, methyl, ethyl, n- or isopropyl, n-, iso-, sec- or tert-butyl.

M stands preferably for one of the following cyclics

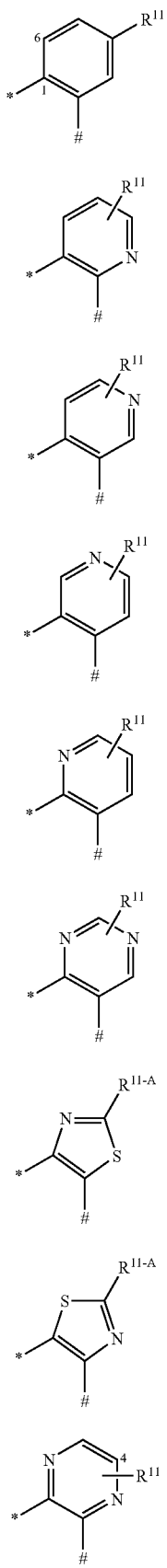

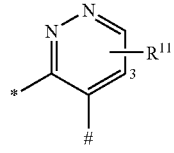

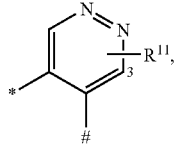

whereby the bond marked with an asterisk ("*") is a link with the amide, and the bond marked with "#" is a link with the haloalkyl group.

M stands particularly preferably for a cyclic selected from M-1, M-2, M-3, M-6, M-7 and M-8.

M stands most particularly preferably for the cyclic M-1.

M furthermore stands most particularly preferably for the heterocycle M-2.

M furthermore stands most particularly preferably for the heterocycle M-3.

M furthermore stands most particularly preferably for the heterocycle M-6.

M furthermore stands most particularly preferably for the heterocycle M-7.

M furthermore stands most particularly preferably for the heterocycle M-8.

R11 stands preferably for hydrogen, fluorine, chlorine, methyl or trifluoromethyl.

$R^{11}$ stands most particularly preferably for hydrogen or chlorine.

$R^{11}$ furthermore stands preferably for fluorine in the case that M stands for M-2, M-3, M-4 or M-5, whereby the fluorine is particularly preferred in the 6-position (M-2, M-3) or in the 3-position (M-4, M-5).

$R^{11}$ furthermore stands preferably for chlorine in the case that M stands for M-2, M-3, M-4 or M-5, whereby the chlorine is particularly preferred in the 6-position (M-2, M-3) or in the 3-position (M-4, M-5).

$R^{11}$ furthermore stands preferably for methyl in the case that M stands for M-2, M-3, M-4 or M-5, whereby the methyl group is particularly preferred in the 4-position (M-2) or in the 3-position (M-3, M-4, M-5).

$R^{11}$ furthermore stands preferably for methyl in the case that M stands for M-6, whereby the methyl group is particularly preferred in the 3-position.

$R^{11}$ furthermore stands preferably for trifluoromethyl in the case that M stands for M-6, whereby the trifluoromethyl group is particularly preferred in the 3-position.

$R^{11}$ furthermore stands preferably for methyl in the case that M stands for M-9, whereby the methyl group is particularly preferred in the 4-position.

$R^{11}$ furthermore stands preferably for trifluoromethyl in the case that M stands for M-9, whereby the trifluoromethyl group is particularly preferred in the 4-position.

$R^{11}$ furthermore stands preferably for methyl in the case that M stands for M-10, whereby the methyl group is particularly preferred in the 3-position.

$R^{11}$ furthermore stands preferably for trifluoromethyl in the case that M stands for M-10, whereby the trifluoromethyl group is particularly preferred in the 3-position.

$R^{11}$ furthermore stands preferably for methyl in the case that M stands for M-11, whereby the methyl group is particularly preferred in the 3-position.

$R^{11}$ furthermore stands preferably for trifluoromethyl in the case that M stands for M-11, whereby the trifluoromethyl group is particularly preferred in the 3-position.

$R^{11-A}$ stands preferably for hydrogen.

$R^{11-A}$ furthermore stands preferably for methyl.

$R^{11-A}$ furthermore stands preferably for trifluoromethyl.

A stands preferably for one of the groups A1, A2, A3, A4, A5, A6, A9, A10, A11, A12, A16 or A17.

A stands particularly preferably for one of the groups A1, A2, A3, A4, A5, A6, A9, A11, A16, A17, A18.

A most particularly preferably stands for the group A1.

A furthermore most particularly preferably stands for the group A2.

A furthermore most particularly preferably stands for the group A3.

A furthermore most particularly preferably stands for the group A4.

A furthermore most particularly preferably stands for the group A5.

A furthermore most particularly preferably stands for the group A6.

A furthermore most particularly preferably stands for the group A9.

A furthermore most particularly preferably stands for the group A11.

A furthermore most particularly preferably stands for the group A16.

A furthermore most particularly preferably stands for the group A17.

A furthermore most particularly preferably stands for the group A18.

$R^{12}$ stands preferably for hydrogen, cyano, fluorine, chlorine, bromine, iodine, methyl, ethyl, isopropyl, methoxy, ethoxy, methylthio, ethylthio, cyclopropyl, $C_1$-$C_2$ haloalkyl, $C_1$-$C_2$ halo alkoxy in each case with 1 to 5 fluorine, chlorine and/or bromine atoms, trifluoromethylthio, difluoromethylthio, aminocarbonyl, aminocarbonylmethyl or aminocarbonylethyl.

$R^{12}$ stands particularly preferably for hydrogen, fluorine, chlorine, bromine, iodine, methyl, ethyl, isopropyl, monofluoromethyl, monofluoroethyl, difluoromethyl, trifluoromethyl, difluoro chloromethyl, trichloromethyl, dichloromethyl, cyclopropyl, methoxy, ethoxy, trifluoro methoxy, trichloromethoxy, methylthio, ethylthio, trifluoromethylthio or difluoromethylthio.

$R^{12}$ stands most particularly preferably for hydrogen, fluorine, chlorine, bromine, iodine, methyl, isopropyl, monofluoromethyl, monofluoroethyl, difluoromethyl, trifluoromethyl, difluorochloromethyl or trichloromethyl.

$R^{12}$ stands p y for methyl, difluoromethyl, trifluoromethyl or 1-fluoroethyl.

$R^{13}$ stands preferably for hydrogen, fluorine, chlorine, bromine, iodine, methyl, ethyl, methoxy, ethoxy, methylthio or ethylthio.

$R^{13}$ stands particularly preferably for hydrogen, fluorine, chlorine, bromine, iodine or methyl.

$R^{13}$ stands most particularly preferably for hydrogen, fluorine, chlorine, or methyl.

$R^{14}$ stands preferably for hydrogen, methyl, ethyl, n-propyl, isopropyl, $C_1$-$C_2$ haloalkyl with 1 to 5 fluorine, chlorine and/or bromine atoms, hydroxymethyl, hydroxyethyl, cyclopropyl, cyclopentyl, cyclohexyl or phenyl.

$R^{14}$ stands particularly preferably for hydrogen, methyl, ethyl, isopropyl, trifluoromethyl, difluoromethyl, hydroxymethyl, hydroxyethyl or phenyl.

$R^{14}$ stands most particularly preferably for hydrogen, methyl, trifluoromethyl or phenyl.

$R^{14}$ stands especially preferably for methyl.

$R^{15}$ and $R^{16}$ stand independently of one another preferably for hydrogen, fluorine, chlorine, bromine, methyl, ethyl or $C_1$-$C_2$ haloalkyl with 1 to 5 fluorine, chlorine and/or bromine atoms.

$R^{15}$ and $R^{16}$ stand independently of one another particularly preferably for hydrogen, fluorine, chlorine, bromine, methyl, ethyl, difluoromethyl, trifluoromethyl, difluorochloromethyl or trichloromethyl.

$R^{15}$ and $R^{16}$ stand independently of one another most particularly preferably for hydrogen, fluorine, chlorine, bromine, methyl, ethyl, difluoromethyl, trifluoromethyl or trichloromethyl.

$R^{15}$ and $R^{16}$ stand in each case for hydrogen.

$R^{17}$ stands preferably for fluorine, chlorine, bromine, cyano, methyl, ethyl, $C_1$-$C_2$ haloalkyl or $C_1$-$C_2$ haloalkoxy in each case with 1 to 5 fluorine, chlorine and/or bromine atoms.

$R^{17}$ stands particularly preferably for fluorine, chlorine, bromine, cyano, methyl, trifluoro methyl, trifluoromethoxy, difluoromethoxy, difluorochloromethoxy or trichloromethoxy.

$R^{17}$ stands most particularly preferably for fluorine, chlorine, bromine, iodine, methyl, trifluoromethyl or trifluoromethoxy.

$R^{17}$ stands especially preferably for methyl.

$R^{18}$ and $R^{19}$ stand independently of one another preferably for hydrogen, fluorine, chlorine, bromine, methyl, ethyl or $C_1$-$C_2$ haloalkyl with 1 to 5 fluorine, chlorine and/or bromine atoms.

$R^{18}$ and $R^{19}$ stand independently of one another particularly preferably for hydrogen, fluorine, chlorine, bromine, methyl, ethyl, difluoromethyl, trifluoromethyl, difluorochloromethyl or trichloromethyl.

$R^{18}$ and $R^{19}$ stand independently of one another most particularly preferably for hydrogen, fluorine, chlorine, bromine, methyl, ethyl, difluoromethyl, trifluoromethyl or trichloromethyl.

$R^{18}$ and $R^{19}$ stand especially preferably in each case for hydrogen.

$R^{20}$ stands preferably for hydrogen, fluorine, chlorine, bromine, methyl, ethyl or $C_1$-$C_2$ haloalkyl with 1 to 5 fluorine, chlorine and/or bromine atoms.

$R^{20}$ stands particularly preferably for hydrogen, fluorine, chlorine, bromine, iodine, methyl or trifluoromethyl.

$R^{20}$ stands most particularly preferably for methyl.

$R^{21}$ stands preferably for hydrogen, fluorine, chlorine, bromine, iodine, hydroxy, cyano, $C_1$-$C_4$ alkyl, $C_1$-$C_2$ haloalkyl, $C_1$-$C_2$ haloalkoxy or $C_1$-$C_2$ haloalkylthio in each case with 1 to 5 fluorine, chlorine and/or bromine atoms.

$R^{21}$ stands particularly preferably for hydrogen, fluorine, chlorine, bromine, iodine, hydroxy, cyano, methyl, ethyl, n-propyl, isopropyl, n-butyl, iso-butyl, sec-butyl, tert-butyl, difluoro methyl, trifluoromethyl, difluorochloromethyl, trichloromethyl, trifluoromethoxy, difluoro methoxy, difluorochloromethoxy, trichloromethoxy, trifluoromethylthio, difluoro methylthio, difluorochloromethylthio or trichloromethylthio.

$R^{21}$ stands most particularly preferably for hydrogen, fluorine, chlorine, bromine, iodine, methyl, difluoromethyl, trifluoromethyl or trichloromethyl.

$R^{21}$ stands especially preferably for iodine, methyl, difluoromethyl or trifluoromethyl.

$R^{22}$ stands preferably for fluorine, chlorine, bromine, iodine, hydroxy, cyano, $C_1$-$C_4$ alkyl, methoxy, ethoxy, methylthio, ethylthio, difluoromethylthio, trifluoromethylthio, $C_1$-$C_2$ haloalkyl or $C_1$-$C_2$ haloalkoxy in each case with 1 to 5 fluorine, chlorine and/or bromine atoms.

$R^{22}$ stands particularly preferably for fluorine, chlorine, bromine, iodine, hydroxy, cyano, methyl, ethyl, n-propyl, isopropyl, n-butyl, iso-butyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{22}$ stands most particularly preferably for fluorine, chlorine, bromine, iodine, methyl, trifluoromethyl, difluoromethyl or trichloromethyl.

$R^{23}$ stands preferably for hydrogen, fluorine, chlorine, bromine, iodine, cyano, $C_1$-$C_4$ alkyl, methoxy, ethoxy, methylthio, ethylthio, $C_1$-$C_2$ haloalkyl or $C_1$-$C_2$ haloalkoxy in each case with 1 to 5 fluorine, chlorine and/or bromine atoms, $C_1$-$C_2$ alkylsulfinyl or $C_1$-$C_2$ alkylsulfonyl.

$R^{23}$ stands particularly preferably for hydrogen, fluorine, chlorine, bromine, iodine, cyano, n-propyl, isopropyl, n-butyl, iso-butyl, sec-butyl, tert-butyl, trifluoromethyl, difluoromethyl, difluorochloromethyl, trichloromethyl, methoxy, ethoxy, methylthio, ethylthio, trifluoro methoxy, difluoromethoxy, difluorochloromethoxy, trichloromethoxy, methylsulfinyl or methylsulfonyl.

$R^{23}$ stands most particularly preferably for hydrogen, fluorine, chlorine, bromine, iodine, n-propyl, isopropyl, n-butyl, iso-butyl, sec-butyl, tert-butyl, trifluoromethyl, difluoromethyl, trichloromethyl, methylsulfinyl or methylsulfonyl.

$R^{23}$ stands especially preferably for hydrogen.

$R^{24}$ stands preferably for methyl, ethyl or $C_1$-$C_2$ haloalkyl with 1 to 5 fluorine, chlorine and/or bromine atoms.

$R^{24}$ stands particularly preferably for methyl, ethyl, trifluoromethyl, difluoromethyl, difluorochloromethyl or trichloromethyl.

$R^{25}$ stands preferably for methyl or ethyl.

$R^{25}$ stands particularly preferably for methyl.

$Q^1$ stands preferably for S (sulfur), $SO_2$ or $CH_2$.

$Q^1$ stands particularly preferably for S (sulfur) or $CH_2$.

$Q^1$ stands most particularly preferably for S (sulfur).

p stands preferably for 0 or 1.

p stands particularly preferably for 0.

$R^{26}$ stands preferably for methyl, ethyl or $C_1$-$C_2$ haloalkyl with 1 to 5 fluorine, chlorine and/or bromine atoms.

$R^{26}$ stands particularly preferably for methyl, ethyl, trifluoromethyl, difluoromethyl, difluorochloromethyl or trichloromethyl.

$R^{26}$ stands most particularly preferably for methyl, trifluoromethyl, difluoromethyl or trichloromethyl.

$R^{27}$ stands preferably for methyl, ethyl or $C_1$-$C_2$ haloalkyl with 1 to 5 fluorine, chlorine and/or bromine atoms.

$R^{27}$ stands particularly preferably for methyl, ethyl, trifluoromethyl, difluoromethyl, difluorochloromethyl or trichloromethyl.

$R^{27}$ stands most particularly preferably for methyl, trifluoromethyl, difluoromethyl or trichloromethyl.

$R^{28}$ and $R^{29}$ stand independently of one another preferably for hydrogen, fluorine, chlorine, bromine, amino, methyl, ethyl or $C_1$-$C_2$ haloalkyl with 1 to 5 fluorine, chlorine and/or bromine atoms.

$R^{28}$ and $R^{29}$ stand independently of one another particularly preferably for hydrogen, fluorine, chlorine, bromine, methyl, ethyl, trifluoromethyl, difluoromethyl, difluorochloromethyl or trichloromethyl.

$R^{28}$ and $R^{29}$ stand independently of one another most particularly preferably for hydrogen, fluorine, chlorine, bromine, methyl, trifluoromethyl, difluoromethyl or trichloromethyl.

$R^{28}$ and $R^{29}$ stand especially preferably in each case for hydrogen.

$R^{30}$ stands preferably for hydrogen, fluorine, chlorine, bromine, iodine, methyl, ethyl or $C_1$-$C_2$ haloalkyl with 1 to 5 fluorine, chlorine and/or bromine atoms.

$R^{30}$ stands particularly preferably for hydrogen, fluorine, chlorine, bromine, iodine, methyl, ethyl, trifluoromethyl, difluoromethyl, difluorochloromethyl or trichloromethyl.

$R^{30}$ stands most particularly preferably for hydrogen, fluorine, chlorine, bromine, methyl, trifluoromethyl, difluoromethyl or trichloromethyl.

$R^{30}$ stands for methyl.

$R^{31}$ and $R^{32}$ stand independently of one another preferably for hydrogen, fluorine, chlorine, bromine, amino, nitro, methyl, ethyl or $C_1$-$C_2$ haloalkyl with 1 to 5 fluorine, chlorine and/or bromine atoms.

$R^{31}$ and $R^{32}$ stand independently of one another particularly preferably for hydrogen, fluorine, chlorine, bromine, nitro, methyl, ethyl, trifluoromethyl, difluoromethyl, difluorochloromethyl or trichloromethyl.

$R^{31}$ and $R^{32}$ stand independently of one another most particularly preferably for hydrogen, fluorine, chlorine, bromine, methyl, trifluoromethyl, difluoromethyl or trichloromethyl.

$R^{31}$ and $R^{32}$ stand especially preferably in each case for hydrogen.

$R^{33}$ stands preferably for hydrogen, fluorine, chlorine, bromine, iodine, methyl, ethyl or $C_1$-$C_2$ haloalkyl with 1 to 5 fluorine, chlorine and/or bromine atoms, $R^{33}$ stands particularly preferably for hydrogen, fluorine, chlorine, bromine, iodine, methyl, ethyl, trifluoromethyl, difluoromethyl, difluorochloromethyl or trichloromethyl.

$R^{33}$ stands most particularly preferably for hydrogen, fluorine, chlorine, bromine, methyl, trifluoromethyl, difluoromethyl or trichloromethyl.

$R^{33}$ stands especially preferably for methyl.

$R^{34}$ stands preferably for hydrogen, fluorine, chlorine, bromine, amino, $C_1$-$C_4$ alkylamino, di($C_1$-$C_4$ alkyl)amino, cyano, methyl, ethyl or $C_1$-$C_2$ haloalkyl with 1 to 5 fluorine, chlorine and/or bromine atoms.

$R^{34}$ stands particularly preferably for hydrogen, fluorine, chlorine, bromine, amino, methylamino, dimethylamino, cyano, methyl, ethyl, trifluoromethyl, difluoromethyl, difluorochloromethyl or trichloromethyl.

$R^{34}$ stands most particularly preferably for hydrogen, fluorine, chlorine, bromine, amino, methylamino, dimethylamino, methyl, trifluoromethyl, difluoromethyl or trichloromethyl.

$R^{34}$ stands especially preferably for amino, methylamino, dimethylamino, methyl or trifluoromethyl.

$R^{35}$ stands preferably for fluorine, chlorine, bromine, methyl, ethyl or $C_1$-$C_2$ haloalkyl with 1 to 5 fluorine, chlorine and/or bromine atoms.

$R^{35}$ stands particularly preferably for fluorine, chlorine, bromine, methyl, ethyl, trifluoromethyl, difluoromethyl, difluorochloromethyl or trichloromethyl.

$R^{35}$ stands most particularly preferably for fluorine, chlorine, bromine, methyl, trifluoromethyl, difluoromethyl or trichloromethyl.

$R^{33}$ stands for methyl, trifluoromethyl or difluoromethyl.

$R^{36}$ stands preferably for hydrogen, fluorine, chlorine, bromine, amino, $C_1$-$C_4$ alkylamino, di($C_1$-$C_4$ alkyl)amino, cyano, methyl, ethyl or $C_1$-$C_2$ haloalkyl with 1 to 5 fluorine, chlorine and/or bromine atoms.

$R^{36}$ stands particularly preferably for hydrogen, fluorine, chlorine, bromine, amino, methylamino, dimethylamino, cyano, methyl, ethyl, trifluoromethyl, difluoromethyl, difluorochloromethyl or trichloromethyl.

$R^{36}$ stands most particularly preferably for hydrogen, fluorine, chlorine, bromine, amino, methylamino, dimethylamino, methyl, trifluoromethyl, difluoromethyl or trichloromethyl.

$R^{36}$ stands especially preferably for amino, methylamino, dimethylamino, methyl or trifluoromethyl.

$R^{37}$ stands preferably for fluorine, chlorine, bromine, methyl, ethyl or $C_1$-$C_2$ haloalkyl with 1 to 5 fluorine, chlorine and/or bromine atoms.

$R^{37}$ stands particularly preferably for fluorine, chlorine, bromine, methyl, ethyl, trifluoromethyl, difluoromethyl, difluorochloromethyl or trichloromethyl.

$R^{37}$ stands most particularly preferably for fluorine, chlorine, bromine, methyl, trifluoromethyl, difluoromethyl or trichloromethyl.

$R^{37}$ stands especially preferably for methyl, trifluoromethyl or difluoromethyl.

$R^{38}$ stands preferably for fluorine, chlorine, bromine, methyl, ethyl or $C_1$-$C_2$ haloalkyl with 1 to 5 fluorine, chlorine and/or bromine atoms.

$R^{38}$ stands particularly preferably for fluorine, chlorine, bromine, methyl, ethyl, trifluoromethyl, difluoromethyl, difluorochloromethyl or trichloromethyl.

$R^{38}$ stands most particularly preferably for fluorine, chlorine, bromine, methyl, trifluoromethyl, difluoromethyl or trichloromethyl.

$R^{39}$ stands preferably for hydrogen, methyl or ethyl.

$R^{39}$ stands particularly preferably for methyl.

$R^{40}$ stands preferably for fluorine, chlorine, bromine, methyl or ethyl, $R^{40}$ stands particularly preferably for fluorine, chlorine, or methyl.

$R^{41}$ stands preferably for methyl, ethyl or $C_1$-$C_2$ haloalkyl with 1 to 5 fluorine, chlorine and/or bromine atoms.

$R^{41}$ stands particularly preferably for methyl, ethyl, trifluoromethyl, difluoromethyl, difluorochloromethyl or trichloromethyl.

$R^{41}$ stands most particularly preferably for methyl, trifluoromethyl, difluoromethyl or trichloromethyl.

$R^{41}$ stands preferably for methyl or trifluoromethyl.

$R^{42}$ stands preferably for hydrogen, fluorine, chlorine, bromine, methyl, ethyl or $C_1$-$C_2$ haloalkyl with 1 to 5 fluorine, chlorine and/or bromine atoms.

$R^{42}$ stands particularly preferably for hydrogen, fluorine, chlorine, bromine, methyl or trifluoromethyl.

$R^{43}$ stands preferably for fluorine, chlorine, bromine, iodine, hydroxy, $C_1$-$C_4$ alkyl, methoxy, ethoxy, methylthio, ethylthio, difluoromethylthio, trifluoromethylthio, $C_1$-$C_2$ haloalkyl or $C_1$-$C_2$ haloalkoxy in each case with 1 to 5 fluorine, chlorine and/or bromine atoms.

$R^{43}$ stands particularly preferably for fluorine, chlorine, bromine, iodine, methyl, ethyl, n-propyl, isopropyl, n-butyl, iso-butyl, sec-butyl, tert-butyl, trifluoromethyl, difluoromethyl, difluorochloromethyl or trichloromethyl.

$R^{43}$ stands most particularly preferably for fluorine, chlorine, bromine, iodine, methyl, trifluoromethyl, difluoromethyl or trichloromethyl.

$R^{44}$ stands preferably for hydrogen, methyl, ethyl, $C_1$-$C_2$ haloalkyl with 1 to 5 fluorine, chlorine and/or bromine atoms, $C_1$-$C_4$ alkoxy-$C_1$-$C_4$-alkyl, hydroxymethyl, hydroxyethyl, methylsulfonyl or dimethylaminosulfonyl.

$R^{44}$ stands particularly preferably for hydrogen, methyl, ethyl, trifluoromethyl, methoxymethyl, ethoxymethyl, hydroxymethyl or hydroxyethyl.

$R^{44}$ stands most particularly preferably for methyl or methoxymethyl.

$R^{45}$ stands preferably for hydrogen, fluorine, chlorine, bromine, methyl, ethyl or $C_1$-$C_2$ haloalkyl with 1 to 5 fluorine, chlorine and/or bromine atoms.

$R^{45}$ stands particularly preferably for hydrogen, fluorine, chlorine, bromine, methyl, ethyl, trifluoromethyl, difluoromethyl, or trichloromethyl.

$R^{45}$ stands most particularly preferably for hydrogen or methyl.

$R^{46}$ stands preferably for hydrogen, fluorine, chlorine, bromine, iodine, cyano, methyl, ethyl, isopropyl or $C_1$-$C_2$ haloalkyl with 1 to 5 fluorine, chlorine and/or bromine atoms.

$R^{46}$ stands particularly preferably for hydrogen, fluorine, chlorine, bromine, iodine, cyano, methyl, ethyl, isopropyl, trifluoromethyl, difluoromethyl, difluorochloromethyl or trichloromethyl.

$R^{46}$ stands most particularly preferably for hydrogen, methyl, difluoromethyl or trifluoromethyl.

$R^{47}$ stands preferably for hydrogen, fluorine, chlorine, bromine, methyl, ethyl or $C_1$-$C_2$ haloalkyl with 1 to 5 fluorine, chlorine and/or bromine atoms.

$R^{47}$ stands particularly preferably for hydrogen, fluorine, chlorine, bromine, iodine, methyl or trifluoromethyl.

$R^{47}$ stands most particularly preferably for hydrogen.

$R^{48}$ stands preferably for methyl, ethyl, n-propyl or isopropyl.

$R^{48}$ stands particularly preferably for methyl or ethyl.

Preferred embodiments are those compounds corresponding to formula (I), in which all groups have the preferred meanings cited above in each case.

Particularly preferred embodiments are those compounds corresponding to formula (I), in which all groups have the particularly preferred meanings cited above in each case.

The following groups of new carboxamides are preferred and each to be considered as a subset of the compounds corresponding to formula (I) cited above:

Group 1: Haloalkyl carboxamides of the formula (I-a)

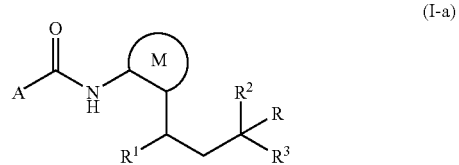

in which R, $R^1$, $R^2$, $R^3$, M and A have the meanings specified above.

Group 2: Haloalkyl carboxamides of the formula (I-b)

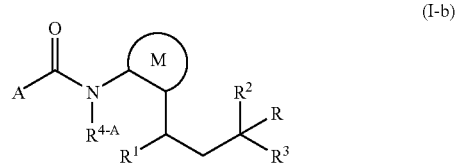

in which R, $R^1$, $R^2$, $R^3$, $R^{4-A}$, M and A have the meanings specified above.

$R^{4-A}$ stands preferably for $C_1$-$C_6$ alkyl, $C_1$-$C_4$ alkylsulfinyl, $C_1$-$C_4$ alkylsulfonyl, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkylthio, $C_1$-$C_4$ haloalkylsulfinyl, $C_1$-$C_4$ haloalkylsulfonyl, halo-$C_1$-$C_3$-alkoxy-$C_1$-$C_3$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$ alkyl)carbonyl-$C_1$-$C_3$-alkyl, ($C_1$-$C_3$ alkoxy)carbonyl-$C_1$-$C_3$-alkyl; halo-($C_1$-$C_3$ alkyl)carbonyl-$C_1$-$C_3$-alkyl, halo-($C_1$-$C_3$ alkoxy)carbonyl-$C_1$-$C_3$-alkyl with 1 to 13 fluorine, chlorine and/or bromine atoms in each case;

($C_1$-$C_6$ alkyl)carbonyl, ($C_1$-$C_4$ alkoxy)carbonyl, ($C_1$-$C_3$-alkoxy-$C_1$-$C_3$-alkyl)carbonyl, ($C_3$-$C_6$ cycloalkyl)carbonyl; ($C_1$-$C_4$ haloalkyl)carbonyl, ($C_1$-$C_4$ haloalkoxy)carbonyl, (halo-$C_1$-$C_3$-alkoxy-$C_1$-$C_3$-alkyl)carbonyl, ($C_3$-$C_6$ halocycloalkyl)carbonyl with 1 to 9 fluorine, chlorine and/or bromine atoms in each case; or —C(=O)C(=O)$R^5$, —CONR$^6$R$^7$ or —CH$_2$NR$^8$R$^9$.

$R^{4-A}$ stands particularly preferably for methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethyl thio, trifluoromethylthio, trifluoromethylsulfinyl, trifluoromethylsulfonyl, trifluoromethoxy methyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoro methylcarbonyl, trifluoromethoxycarbonyl, or —C(=O)C(=O)$R^5$, —CONR$^{67}$ or —CH$_2$NR$^8$R$^9$.

$R^{4-A}$ stands most particularly preferably for methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

Group 3: Haloalkyl carboxamides of the formula (I-c)

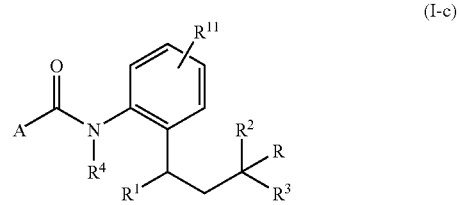

(I-c)

in which R, $R^1$, $R^2$, $R^3$, $R^4$, $R^{11}$ and A have the meanings specified above.

Preferred embodiments are haloalkyl carboxamides of the formula (I-c), in which $R^4$ stands for hydrogen.

Preferred embodiments are haloalkyl carboxamides of the formula (I-c), in which $R^{11}$ stands for hydrogen.

Preferred embodiments are haloalkyl carboxamides of the formula (I-c), in which $R^4$ and $R^{11}$ each stand for hydrogen.

Group 4: Haloalkyl carboxamides of the formula (I-d)

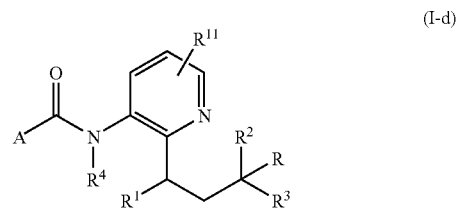

(I-d)

in which R, $R^1$, $R^2$, $R^3$, $R^4$, $R^{11}$ and A have the meanings specified above.

Preferred embodiments are haloalkyl carboxamides of the formula (I-d), in which $R^4$ stands for hydrogen.

Preferred embodiments are haloalkyl carboxamides of the formula (I-d), in which $R^{11}$ stands for hydrogen.

Preferred embodiments are haloalkyl carboxamides of the formula (I-d), in which $R^4$ and $R^{11}$ each stand for hydrogen.

Group 5: Haloalkyl carboxamides of the formula (I-e)

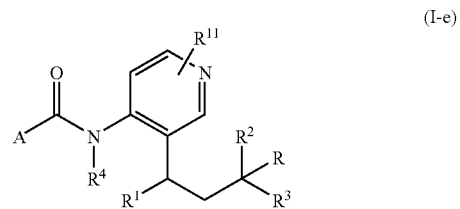

(I-e)

in which R, $R^1$, $R^2$, $R^3$, $R^4$, $R^{11}$ and A have the meanings specified above.

Preferred embodiments are haloalkyl carboxamides of the formula (I-e), in which $R^4$ stands for hydrogen.

Preferred embodiments are haloalkyl carboxamides of the formula (I-e), in which $R^{11}$ stands for hydrogen.

Preferred embodiments are haloalkyl carboxamides of the formula (I-e), in which $R^4$ and $R^{11}$ each stand for hydrogen.

Group 6: Haloalkyl carboxamides of the formula (I-f)

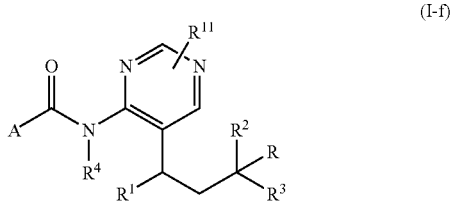

(I-f)

in which $R^1$, $R^1$, $R^2$, $R^3$, $R^4$, $R^{11}$ and A have the meanings specified above.

Preferred embodiments are haloalkyl carboxamides of the formula (I-f), in which $R^4$ stands for hydrogen.

Preferred embodiments are haloalkyl carboxamides of the formula (I-f), in which $R^{11}$ stands for hydrogen.

Preferred embodiments are haloalkyl carboxamides of the formula (I-f), in which R4 and R11 each stand for hydrogen.

Group 7: Haloalkyl carboxamides of the formula (I-g)

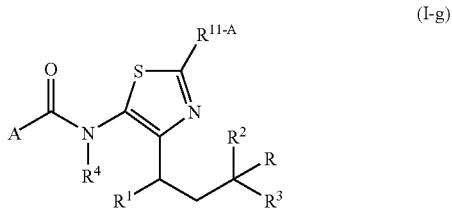

(I-g)

in which R, $R^1$, $R^2$, $R^3$, $R^4$, $R^{11\text{-}A}$ and A have the meanings specified above.

Preferred embodiments are haloalkyl carboxamides of the formula (I-g), in which $R^4$ stands for hydrogen.

Preferred embodiments are haloalkyl carboxamides of the formula (I-g), in which $R^{11}$ stands for hydrogen.

Preferred embodiments are haloalkyl carboxamides of the formula (I-g), in which $R^4$ and $R^{11\text{-}A}$ each stand for hydrogen.

Group 8: Haloalkyl carboxamides of the formula (I-h)

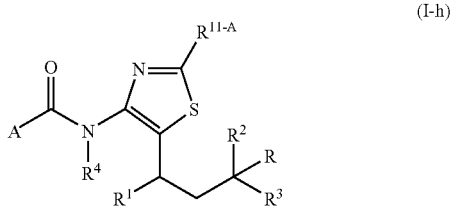

(I-h)

in which R, $R^1$, $R^2$, $R^3$, $R^4$, $R^{11\text{-}A}$ and A have the meanings specified above.

Preferred embodiments are haloalkyl carboxamides of the formula (I-h), in which $R^4$ stands for hydrogen.

Preferred embodiments are haloalkyl carboxamides of the formula (I-h), in which $R^{11}$ stands for hydrogen.

Preferred embodiments are haloalkyl carboxamides of the formula (I-h), in which $R^4$ and $R^{11\text{-}A}$ each stand for hydrogen.

Compounds of the formula (I) (and likewise of the groups 1 to 8), in which $R^4$ stands for hydrogen are emphasized.

Compounds of the formula (I) (and likewise of the groups 1 to 8), in which $R^4$ stands for formyl are emphasized.

Furthermore, compounds of the formula (I) (and likewise of the groups 1 to 8), in which $R^4$ stands for —C(=O)C(=O)$R^5$ are emphasized, whereby $R^5$ has the meanings specified above.

Saturated or unsaturated hydrocarbon groups, such as alkyl or alkenyl, also in combination with hetero atoms, such as, for example, in alcoxy, can each be straight-chained or branched to the extent that is possible.

Possibly substituted groups can be singly or multiply substituted, whereby with multiple substitutions, the substitutents can be the same or varied. Thus the definition "dialkylamino" also includes an asymmetrically substituted amino group, such as, for example, methyl ethyl amino.

Halogen-substituted groups, such as, for example, haloalkyl, are singly or multiply halogenated. With multiple halogenation, the halogen atoms can be the same or different. Halogen in this case stands for fluorine, chlorine, bromine and iodine, particularly for fluorine, chlorine and bromine.

The general or preferential group definitions and/or explanations listed above can be combined arbitrarily between the respective areas and preferential areas. They apply to end products as well as correspondingly to preliminary and intermediate products. Especially the compounds named in the groups 1 to 6 can be combined both with the general as well as the preferred, particularly preferred, etc. definitions, whereby here as well all combinations of the preferred areas are possible in each case.

Description of the Inventive Process for the Synthesis of Hexylcarboxanilides of the Formula (I) as Well as the Intermediate Products.

Process (a)

If 2-trifluoromethylbenzoyl chloride and 4-chloro-2-(4,4,4-trifluoro-3-methylbutyl)-phenylamine are used as starting materials, then the inventive process (a) can be illustrated by the following formula diagram:

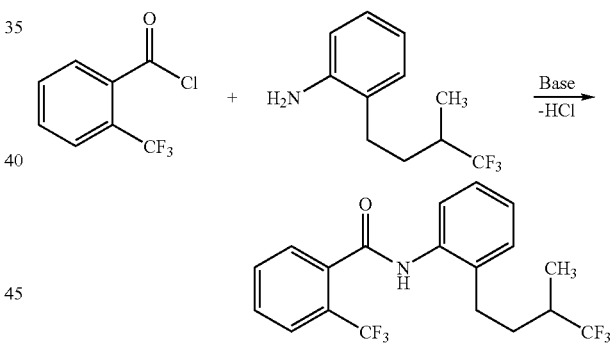

The carboxylic acid derivatives required as starting materials to carry out the inventive process (a) are defined in general by the formula (II). In formula (II), A has the preferred, particularly preferred or most particularly preferred meanings already specified as preferred, particularly preferred or most particularly preferred for A in connection with the description of the inventive compounds according to formula (I). $X^1$ stands preferably for chlorine, bromine or hydroxy.

The carboxylic acid derivatives of the formula (II) are known for the most part and/or maybe synthesized according to known procedures (see WO 93/11117, EP-A 0 545 099, EP-A 0 589 301 and EP-A 0 589 313).

The aniline derivatives further required as starting materials to carry out the inventive process (a) are defined in general by the formula (III). In formula (III), R, $R^1$, $R^2$, $R^3$, $R^4$ and M have the preferred, particularly preferred or most particularly preferred meanings already specified as preferred, particularly preferred or most particularly preferred for these groups in connection with the description of the inventive compounds according to formula (I).

The aniline derivatives of the formula (III) are new.

Aniline derivatives of the formula (III-a)

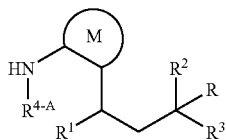

in which R, $R^1$, $R^2$, $R^3$, $R^{4-A}$ and M have the meanings specified above, are obtained by reacting c) aniline derivatives of the formula (III-b)

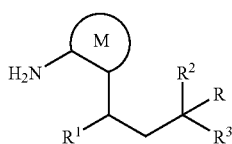

in which R, $R^1$, $R^2$, $R^3$ and M have the meanings specified above, with halides of the formula (IV)

 (IV)

in which $R^{4-A}$ and $X^2$ have the meanings specified above, in the presence of a base and in the presence of a dilution medium.

Aniline derivatives of the formula (III-c)

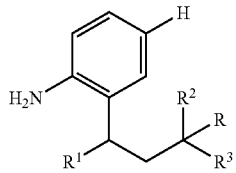

in which R, $R^1$, $R^2$ and $R^3$ have the meanings specified above, are obtained by reacting d) Aniline derivatives of the formula (III-d)

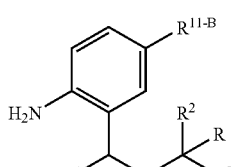

in which
R, $R^1$, $R^2$ and $R^3$ have the meanings specified above,
$R^{11-B}$ stands for fluorine or chlorine,
in the presence of a reducing agent, a catalyst and a dilution medium.

Aniline derivatives of the formula (III-e)

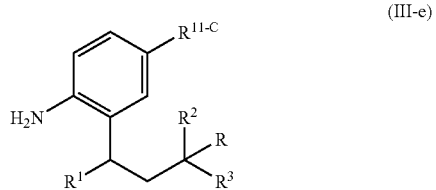

in which
R, $R^2$ and $R^3$ have the meanings specified above and
$R^{11-C}$ stands for fluorine, chlorine, methyl, isopropyl, methylthio or trifluoromethyl, are obtained by reacting e) haloalkyl ketoanilines of the formula (V)

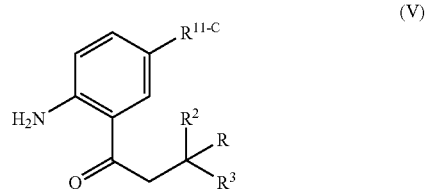

in which R, $R^2$, $R^3$ and $R^{11-C}$ have the meanings specified above, with hydrazine or hydrazine hydrate in the presence of a base (for example alkali or alkaline earth metal hydroxides such as sodium hydroxide or potassium hydroxide) and possibly in the presence of a dilution medium Haloalkyl ketoanilines of the formula (V)

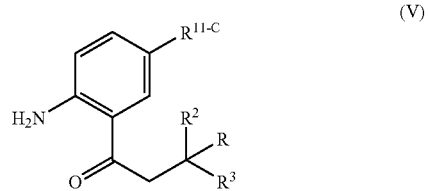

in which R, $R^2$, $R^3$ and $R^{11-C}$ have the meanings specified above, are obtained by reacting f) protected haloalkyl ketoanilines of the formula (VI)

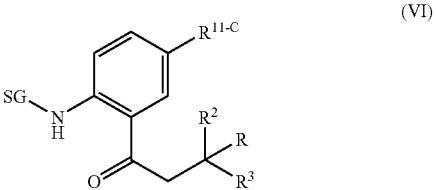

in which
R, $R^2$, $R^3$ and $R^{11-C}$ have the meanings specified above and
SG stands for a protective group, preferably Piv (tert-butylcarbonyl), Boc (tert butoxycarbonyl), Cbz (benzyloxycarbonyl), trifluoroacetyl, Fmoc (9-fluoroenyl-methoxycarbonyl) or Troc (2,2,2-trichlorethoxycarbonyl), in the presence of an acid (such as hydrochloric acid) and possibly in the presence of a dilution medium.

Protected haloalkyl ketoanilines of the formula (VI)

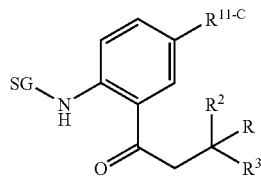
(VI)

in which R, $R^2$, $R^3$, $R^{11-C}$ and SG have the meanings specified above, are obtained by reacting
g) protected anilines of the formula (VII)

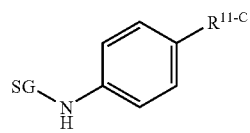
(VII)

in which $R^{11-C}$ and SG have the meanings specified above, with an ester of the formula (VIII)

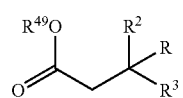
(VIII)

in which
R, $R^2$ and $R^3$ have the meanings specified above,
$R^{49}$ stands for $C_1$-$C_4$ alkyl, preferably methyl or ethyl, in the presence a dilution medium and organometallic bases.

Protected anilines of the formula (VII) and esters of the formula (VIII) are known.

Aniline derivatives of the formula (III-f)

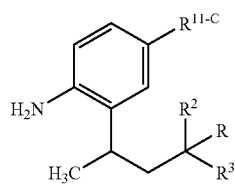
(III-f)

in which
R, $R^2$, $R^3$ and $R^{11-C}$ have the meanings specified above, are obtained by hydrogenating
h) alkenes of the formula (IX)

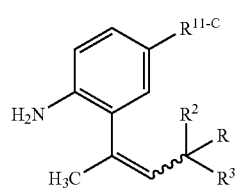
(IX)

in which R, $R^2$, $R^3$ and $R^{11-C}$ have the meanings specified above, possibly in the presence of a dilution medium and possibly in the presence of a catalyst.

Alkenes of the formula (IX)

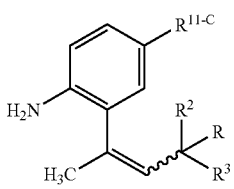
(IX)

in which R, $R^2$, $R^3$ and $R^{11-C}$ have the meanings specified above, are obtained by dehydrating
i) hydroxyalkylanilines of the formula (X)

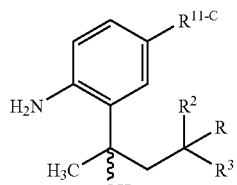
(X)

in which R, $R^2$, $R^3$ and $R^{11-C}$ have the meanings specified above, possibly in the presence of a dilution medium and possibly in the presence of an acid.

Hydroxyalkylanilines of the formula (X)

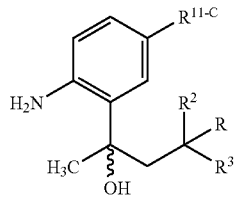
(X)

in which R, $R^2$, $R^3$ and $R^{11-C}$ have the meanings specified above, are obtained by reacting
k) haloalkyl ketoanilines of the formula (V)

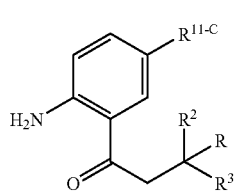
(V)

in which R, $R^2$, $R^3$ and $R^{11-C}$ have the meanings specified above,
with organometallic compounds (such as methylmagnesium halides) in the presence a dilution medium.

Aniline derivatives of the formula (III-g)

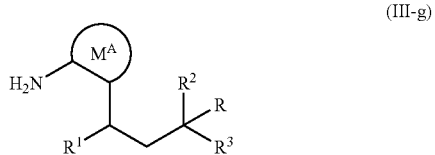

(III-g)

in which

R, $R^1$, $R^2$ and $R^3$ have the meanings specified above and $M^A$ stands in each case for a pyridine or pyrimidine ring with a single substitution by $R^{11}$ or for a thiazole ring substituted with a single substitution by $R^{11-A}$, can be obtained in an analogous manner or by known processes (see EP-A 0 737 682).

Process (b)

If 3-(difluoromethyl)-1-methyl-N-[2-(4,4,4-trifluoro-3-methylbutyl)phenyl]-1H-pyrazole-4-carboxamide and ethyl-chloro(oxo)acetate are used as starting materials, then the course of the inventive process (b) can be illustrated by the following formula diagram:

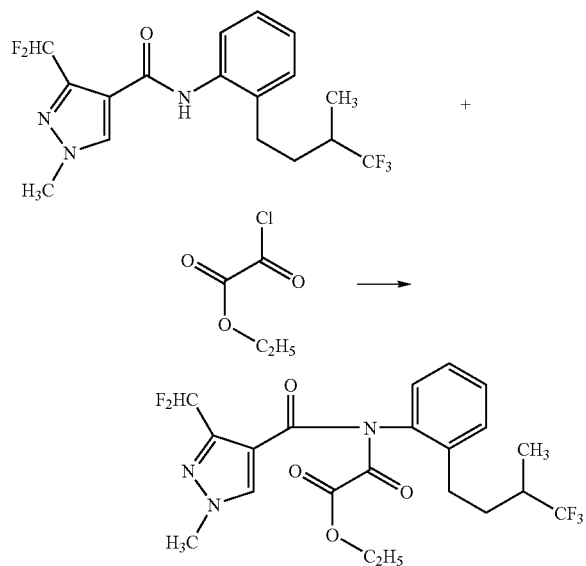

The hexylcarboxanilides required as starting materials to carry out the inventive process (b) are defined in general by the formula (I-a). In formula (I-a), R, $R^1$, $R^2$, $R^3$, M and A have the preferred, particularly preferred or most particularly preferred meanings already specified as preferred, particularly preferred or most particularly preferred for these groups in connection with the description of the inventive compounds according to formula (I).

The hexylcarboxanilides of the formula (I-a) are likewise inventive compounds and subjects of this application. They can be obtained according to the inventive process (a) (with $R^1$=hydrogen).

The halides required as starting materials to carry out the inventive process (b) are defined in general by the formula (IV). In this formula (IV), $R^{4-A}$ has the preferred, particularly preferred or most particularly preferred meanings already specified as preferred, particularly preferred or most particularly preferred for this group in connection with the description of the inventive compounds according to formula (I-b). $X^2$ stands preferably for chlorine or bromine.

Halides of the formula (IV) are known.

Reaction Conditions

All inert organic solvents can be considered as dilution media for carrying out the inventive process (a). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichloro benzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethyl formamide, N,N-dimethyl acetamide, N-methylformanilide, N-methylpyrrolidone or hexamethyl phosphoric acid triamide.

The inventive process (a) is carried out in the presence of a suitable acid acceptor as necessary. All common inorganic or organic bases can be used for this purpose. These include preferably alkaline earth metal hydrides or alkali metal hydrides, hydroxides, amides, alkoxides, acetates, carbonates or hydrogen carbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, as well as tertiary amines, such as trimethylamine, triethylamine, tributyl amine, N,N-dimethylaniline, N,N-dimethyl benzyl amine, pyridine, N-methyl piperidine, N-methyl morpholine, N,N-dimethylaminopyridine, diazabicyclooctane (DABCO), diazabicyclononene (DBN) or diazabicycloundecene (DBU).

The inventive process (a) is carried out in the presence of a suitable condensation agent as necessary. Condensation agents to be considered are those typically used for such amidation reactions. Named as examples are reagents that form acid halides, such as phosgene, phosphorus tribromide, phosphorus trichloride, phosphorus pentachloride, phosphorus oxychloride or thionyl chloride; reagents that form anhydrides such as chloroformic acid ethyl ester, chloroformic acid methyl ester, chloroformic acid isopropyl ester, chloroformic acid isobutyl ester or methane sulfonyl chloride; carbodiimides, such as N,N'-dicyclohexylcarbodiimide (DCC) or other common condensation agents, such as phosphorus pentoxide, polyphosphoric acid, N,N'-carbonyldiimidazole, 2-ethoxy-1-ethoxycarbonyl-1,2-dihydroquinoline (EEDQ), triphenylphosphine/tetrachloromethane or bromotripyrrolidinophosphonium hexafluorophosphate.

The inventive process (a) is carried out in the presence of a catalyst as necessary. Named as examples are 4-dimethylaminopyridine, 1-hydroxybenzotriazole or dimethyl formamide.

In carrying out the inventive process (a), the reaction temperatures can be varied over a wide range. Generally one works at temperatures of 0° C. to 150° C., preferably at temperatures of 0° C. to 80° C.

To carry out the inventive process (a) for the synthesis of compounds of the formula (I), generally 0.2 to 5 mols, preferably 0.5 to 2 mols, of an aniline derivative of the formula (III) are used per mol of the carboxylic acid derivative of the formula (II).

All inert organic solvents can be considered as dilution media for carrying out the inventive processes (b) and (c). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethyl formamide, N,N-dimethyl acetamide, N-methylformanilide, N-methylpyrrolidone or hexamethyl phosphoric acid triamide.

The inventive processes (b) and (c) are carried out in the presence of a base. All common inorganic or organic bases can be used for this purpose. These include preferably alkaline earth metal hydrides or alkali metal hydrides, hydroxides, amides, alkoxides, acetates, carbonates or hydrogen carbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or cesium carbonate, as well as tertiary amines, such as trimethylamine, triethylamine, tributylamine, N,N-dimethylaniline, N,N-dimethyl benzyl amine, pyridine, N-methyl piperidine, N-methyl morpholine, N,N-dimethylaminopyridine, diazabicyclooctane (DABCO), diazabicyclononene (DBN) or diazabicycloundecene (DBU).

In carrying out the inventive processes (b) and (c), the reaction temperatures can be varied over a wide range. Generally one works at temperatures of 0° C. to 150° C., preferably at temperatures of 20° C. to 110° C.

To carry out the inventive process (b) for the synthesis of compounds corresponding to formula (I), generally 0.2 to 5 mols, preferably 0.5 to 2 mols, of a halide of the formula (IV) are used per mol of the hexylcarboxanilide of the formula (I-a).

To carry out the inventive process (c) for the synthesis of compounds of the formula (III-a), generally 0.2 to 5 mols, preferably 0.5 to 2 mols, of a halide of the formula (IV) are used per mol of the aniline derivative of the formula (III-b).

All inert organic solvents can be considered as dilution media for carrying out the inventive process (d). This preferably includes aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; amides, such as N,N-dimethyl formamide, N,N-dimethyl acetamide, N-methylformanilide, N-methylpyrrolidone or hexamethyl phosphoric acid triamide; sulfoxides, such as dimethyl sulfoxide; sulfones, such as sulfolan; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, their mixtures with water or pure water.

The inventive process (d) is carried out in the presence of a metal. Preference is given here to transition metals, such as, for example, palladium, platinum, rhodium, nickel, iron, cobalt, ruthenium, iridium or osmium. The metals can be bound to a substrate as needed, such as, for example, carbon, resins, zeolites, alkali or alkaline earth sulfates.

The inventive process (d) is carried out in the presence of a reducing agent. Materials preferred for this are elemental hydrogen, formate salts, preferably alkali formate salts, such as, for example sodium formate, but also ammonium formate or also metal hydrides (hydrodehalogenation).

The inventive process (d) can be carried out in the presence of acids. Materials preferred for this are organic acids, such as, for example, formic acid, acetic acid, ascorbic acid, but also inorganic acids, such as, for example, hydrochloric acid or sulfuric acid.

The inventive process (d) can be carried out in the presence of bases. Materials preferred for this are organic bases, such as, for example, pyridine, aber also aqueous solutions of alkali or alkaline earth metal hydroxides, such as, for example, sodium hydroxide or barium hydroxide.

In carrying out the inventive process (d), the reaction temperatures can be varied over a wide range. Generally one works at temperatures of −80° C. to 300° C., preferably at temperatures of 0° C. to 200° C.

With the use of elemental hydrogen, the inventive process (d) is carried out in hydrogen pressure between 0.5 and 200 bar, preferably between 1 and 100 bar.

To carry out the inventive process (e) for the synthesis of compounds of the formula (III-c), generally 0.8 to 1000 mols, preferably 1 to 500 mols, of a reducing agent (ammonium formate, hydride, etc.) are used per mol of an aniline derivative of the formula (III-d).

All inert organic solvents can be considered as diluents for carrying out the inventive process (e). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or iso-butyronitrile or benzonitrile; amides, such as N,N-dimethyl formamide, N,N-dimethyl acetamide, N-methylformanilide, N-methylpyrrolidone or hexamethyl phosphoric acid triamide; sulfoxides, such as dimethyl sulfoxide; sulfones, such as sulfolan; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, their mixtures with water or pure water.

The inventive process (e) is carried out in the presence of a base. Materials preferred for this include alkaline earth metal or alkali metal hydroxides, such as, for example, sodium hydroxide, potassium hydroxide, ammonium hydroxide.

In carrying out the inventive process (e), the reaction temperatures can be varied over a wide range. Generally one works at temperatures of 100° C. to 300° C., preferably at temperatures of 150° C. to 250° C.

To carry out the inventive process (e) for the synthesis of compounds of the formula (II-e), generally 0.2 to 5 mols, preferably 0.5 to 3 mols, of hydrazine or hydrazine hydrate are used per mol of the haloalkyl ketoaniline of the formula (V).

All inert organic solvents can be considered as diluents for carrying out the inventive process (f). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethyl formamide, N,N-dimethyl acetamide, N-methylformanilide, N-methylpyrrolidone or hexamethyl phosphoric acid triamide; sulfoxides, such as dimethyl sulfoxide; sulfones, such as sulfolan; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, their mixtures with water or pure water.

The inventive process (f) is carried out in the presence of an acid. Materials preferred for this include inorganic acids, such as, for example, hydrochloric acid, hydroiodic or hydrobromic acid and sulfuric acid or also organic acids, such as trifluoroacetic acid and trifluoromethanesulfonic acid.

In carrying out the inventive process (f), the reaction temperatures can be varied over a wide range. Generally one works at temperatures of 0° C. to 300° C., preferably at temperatures of 20° C. to 200° C.

To carry out the inventive process (f) for the synthesis of compounds of the formula (V), generally 0.1 to 10000 mols, preferably 1 to 2000 mols, of an acid are used per mol of the protected haloalkyl ketoaniline of the formula (VI).

All inert organic solvents can be considered as diluents for carrying out the inventive process (g). This preferably includes aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole.

The inventive process (g) is carried out in the presence of an organometallic compound. Materials preferred for this include organolithium compounds, such as n-, sec-, or tert-butyl lithium, phenyl lithium or methyl lithium.

In carrying out the inventive process (g), the reaction temperatures can be varied over a wide range. Generally one works at temperatures of −120° C. to 100° C., preferably at temperatures of −80° C. to 20° C.

To carry out the inventive process (g) for the synthesis of compounds of the formula (VI), generally 0.2 to 5 mols, preferably 0.5 to 2 mols, of an ester of the formula (VIII) are used per mol of the protected aniline of the formula (VII).

All inert organic solvents can be considered as diluents for carrying out the inventive process (h). This preferably includes aliphatic or alicyclic hydrocarbons, such as, for example, petroleum ether, hexane, heptane, cyclohexane, methylcyclohexane or decalin; ethers, such as diethyl ether, diisopropyl ether, methyl tert-butyl ether, methyl tert-amyl ether, dioxane, tetrahydrofuran, 1,2-dimethoxyethane or 1,2-diethoxyethane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The inventive process (h) is carried out in the presence of a catalyst as necessary. All catalysts typically used for hydrogenation can be used. Examples include: Raney nickel, palladium or platinum, possibly on a substrate, such as, for example, activated carbon.

The hydrogenation in the inventive process (h) can also be carried out in the presence of triethylsilane instead of hydrogen and a catalyst.

In carrying out the inventive process (h), the reaction temperatures can be varied over a wide range. Generally one works at temperatures of 0° C. to 150° C., preferably at temperatures of 20° C. to 100° C.

The inventive process (h) is carried out at a hydrogen pressure between 0.5 and 200 bar, preferably between 2 and 50 bar, particularly preferably between 3 and 10 bar.

All inert organic solvents can be considered as diluents for carrying out the inventive process (i). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or iso-butyronitrile or benzonitrile; amides, such as N,N-dimethyl formamide, N,N-dimethyl acetamide, N-methylformanilide, N-methylpyrrolidone or hexamethyl phosphoric acid triamide; esters, such as methyl acetate or ethyl acetate; sulfoxides, such as dimethyl sulfoxide; sulfones, such as sulfolan; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The inventive process (i) is carried out in the presence of an acid. All inorganic and organic protic acids and Lewis acids, as well as all polymeric acids can be used. These include, for example, hydrogen chloride, sulfuric acid, phosphoric acid, formic acid, acetic acid, trifluoroacetic acid, methanesulfonic acid, trifluoromethanesulfonic acid, toluencesulfonic acid, boron trifluoride (also in etherate form), boron tribromide, aluminum trichloride, titanium tetrachloride, tetrabutyl orthotitanate, zinc chloride, iron (III) chloride, antimony pentachloride, acidic ion exchangers, acid clays and acidic silica gel.

In carrying out the inventive process (i), the reaction temperatures can be varied over a wide range. Generally one works at temperatures of 0° C. to 150° C., preferably at temperatures of 0° C. to 80° C.

The inventive processes (i) and (h) can also be carried out in a tandem (single pot) reaction. To this end, a compound of the formula (X) is reacted in the presence of triethylsilane, possibly in the presence of a dilution medium (suitable solvents for process (i)), possibly in the presence of an acid (acids suitable for process (i)).

All inert organic solvents can be considered as diluents for carrying out the inventive process (k). This preferably includes aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole.

The inventive process (k) is carried out in the presence of an organometallic compound. Materials preferred for this include methylmagnesium chloride, bromide, or iodide or methyl lithium.

In carrying out the inventive process (k), the reaction temperatures can be varied over a wide range. Generally one works at temperatures of −120° C. to 200° C., preferably at temperatures of −80° C. to 100° C.

To carry out the inventive process (k) for synthesizing compounds of the formula (X), generally 0.8 to 10 mols, preferably 1 to 5 mols, of an organometallic compound are used per mol of the haloalkyl ketoaniline of the formula (V).

Unless otherwise specified, all inventive processes are generally carried out at normal pressure. However, is also possible to work under increased or reduced pressure—generally between 0.1 bar and 10 bar.

The inventive materials show strong microbicidal activity and can be used to combat undesired microorganisms, such as fungi and bacteria, in crop protection and material protection.

Fungicides can be used in crop protection to combat Plasmodiophoromycetes, Oomycetes, Chytridiomycetes, Zygomycetes, Ascomycetes, Basidiomycetes and Deuteromycetes.

Bactericides can be used in crop protection to combat Pseudomonadaceae, Rhizobiaceae, Enterobacteriaceae, Corynebacteriaceae and Streptomycetaceae.

Examples of some pathogens of fungal and bacterial diseases that fall under the superordinate terms listed above include, but are not limited to:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae;*

*Pseudocercosporella* species, such as, for example, *Pseudocercosporella herpotrichoides,*

*Rhizoctonia* species, such as, for example, *Rhizoctonia solani.*

The inventive active substances also show a considerable strengthening effect in plants. Thus they are suited for mobilization of the plants' own defenses against infestation by undesirable microorganisms.

In this context, plant-strengthening (resistance-inducing) materials are to be considered those substances that are able to stimulate the immune system of plants such that the plants treated show extensive resistance against undesired microorganisms when subsequently inoculated with these microorganisms.

In the present context, undesired microorganisms are to be understood as phytopathogenic fungi, bacteria and viruses. The inventive materials can also be used to protect plants against infestation by the pathogens cited for a certain period after treatment. The period during which this protection is provided generally lasts from one to 10 days, preferably one to seven days after treatment of the plants with the active substances.

The active substances show good compatibility with plants at the concentrations needed to combat plant diseases, enabling treatment of above-ground plant parts, plant seed stock and soil.

In this regard, the inventive active substances can be used with particularly good success to combat diseases of grain, such as, for example, those caused by *Puccinia* species, and of diseases in the vinoculture, fruit and vegetable farming, such as, for example, those caused by *Botrytis, Venturia* or *Alternaria* species.

The inventive active substances are also suited for increasing harvest yields. Furthermore, they have low toxicity and show good compatibility with plants.

If necessary, at particular concentrations and application rates, the inventive active substances can also be used as herbicides, influencers of plant growth, as well as to fight animal pests. They can also be used as intermediates and starting products for synthesizing other active substances.

All plants and plant parts can be treated in accordance with the invention. As plants in this context, all plants and plant populations are meant, such as desirable wild plants and undesired wild plants (weeds) or cultured plants (including natural occurring cultured plants). Cultured plants can be plants that can be obtained through conventional breeding and optimization methods or through methods of biotechnology and gene technology or a combination of these methods, including transgenic plants and including those plant types which may be eligible or not be eligible for plant variety protection under law. Plant parts should be understood as all above-ground and subterranean parts and organs of plants, such as sprout, leaf, flower and root, whereby, for example, leaves, needles, stalks, stems, flowers, fruiting bodies, fruits and seeds as well as roots, tubers and rhizomes are listed. Plant parts also include harvest product as well as vegetative and generative propagation material, such as cuttings, tubers, rhizomes, scions and seeds.

The treatment of plants and plant parts with the active substances in accordance with the invention is done directly or by acting on their environment, habitat or storage space by conventional treatment methods, such as by immersion, spraying, vapor exposure, fogging, scattering, spreading and by propagation material, particularly seeds, furthermore by single or multi-layered coverage.

In material protection, the inventive materials can be used to protect technical materials against infestation and destruction by undesirable microorganisms.

Technical materials in this context are to be understood as non-living materials for use in technology. For example, technical materials that are to be protected from microbial change or destruction by active substances according to the invention can be adhesives, glues, paper and cardboard, textiles, leather, wood, paints and plastic articles, cooling lubricants and other materials that can be infested or destroyed by microorganisms. Parts of production systems that can be adversely affected by an increase of microorganisms, such as cooling water circuits, also fall within the scope of materials to be protected. Technical materials within the scope of the present invention include preferably adhesives, glues, papers and cardboards, leather, wood, paints, cooling lubricants and heat transfer fluids, particularly preferably wood.

Microorganisms that can effect degradation or a change in technical materials include, for example, include bacteria, fungi, yeasts, algae and slime organisms. The inventive active substances act preferentially against fungi, especially molds, wood-discoloring and wood-destroying fungi (Basidiomycetes) as well as against slime organisms and algae.

The following genera of microorganisms are named as examples:
Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

The active substances can be compounded, depending on their particular physical and/or chemical properties, in typical formulations, such as solutions, emulsions, suspensions, powders, foams, pastes, granulates, aerosols, microencapsulations in polymeric materials and in coatings for seeds, as well as ultra-low volume cold and warm fog formulations.

These formulations are produced according to known methods, such as by mixing the active substances with extenders, i.e. liquid solvents, pressurized, liquified gases and/or solid carrier materials, if necessary with the use of surface-active materials, i.e. emulsifiers and/or dispersing agents and/or foam-producing materials. In the case that water is used as an extender, organic solvents can also be used as solubility aids for example. The following liquid solvents are the main ones to be considered: aromatics, such as xylene, toluene or alkyl naphthalene, chlorinated aromatics or chlorinated aliphatic hydrocarbons, such as chlorobenzenes, chloroethylenes or methylene chloride, aliphatic hydrocarbons, such as cyclohexane or paraffins, such as petroleum fractions, alcohols, such as butanol or glycol as well as their ethers and esters, ketones, such as acetone, methyl ethyl ketone, methyl isobutyl ketone or cyclohexanone, strongly polar solvents, such as dimethyl formamide and dimethyl sulfoxide, as well as water. Liquified gas extenders or carriers are liquids that are gases at normal temperature and normal pressure, for example aerosol propellants, such as halogenated hydrocarbons, as well as butane, propane, nitrogen and carbon dioxide.

Solid carriers to be considered for are, for example, natural mineral powders, such as kaolines, clays, talc, chalk, quartz, attapulgite, montmorillonite or diatomaceous earth and synthetic mineral powders, such as highly disperse silica, aluminum oxide and silicates. Solid carriers to be considered for granulates are, for example, crushed and fractionated natural minerals such as calcite, pumice, marble, sepiolite, dolomite as well as synthetic granulates from inorganic and organic powders as well as granulates from organic material such as sawdust, coconut shells, corn cobs and tobacco stalks. Emulsifiers and/or foam-producing materials to be considered are, for example, non-ionizable and anionic emulsifiers, such as polyoxyethylene-fatty acid esters, polyoxyethylene-fatty alcohol ethers, such as alkyl aryl polyglycol ethers, alkyl sulfonates, alkyl sulfates, aryl sulfonates as well as protein hydrolysates. Dispersing agents to be considered are, for example, lignin, sulfite waste liquors and methyl cellulose.

Formulations can also include bonding agents like carboxymethyl cellulose, natural and synthetic polymers in powdered, granular or latex-like form, such as gum arabic, polyvinyl alcohol, polyvinyl acetate, as well as natural phospholipids, such as cephalins and lecithins, and synthetic phospholipids. Other additives can be mineral and vegetable oils.

Dyes, such as inorganic pigments, for example iron oxide, titanium oxide, Prussian blue and organic dyes, such as alizarin, azo and metal phthalocyanine dyes and trace elements, such as salts of iron, manganese, boron, copper, cobalt, molybdenum and zinc can be used.

The formulations usually contain between 0.1 and 95 weight percent of the active substance, preferably between 0.5 and 90%.

The inventive active substances can be used as such or in their formulations, also mixed with known fungicides, bactericides, akacaricides, nematicides or insecticides, in order, for example, to increase the spectrum of effectiveness or prevent the development of resistances. In many cases, synergistic effects are achieved, i.e. the effectiveness of the mixture is greater than the effectiveness of the individual components.

Examples of complementary formulation components include the following.

Fungicides:
2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benalaxyl-M; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butyl amine; calcium polysulfide; capsimycin; captafol; captan; carbendazim; carboxin; carpropamide; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl- Al; fosetyl-sodium; fuberidazole; furalaxyl; furametpyr; furcarbanil; furnecyclox; guazatine; hexachlorobenzene; hexaconazole; hymexazol; imazalil; imibenconazole; iminoctadine triacetate; iminoctadine albesilate; iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propinyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl) pyridine; 2-amino-4-methyl-N-phenyl-5-thiazolecarboxamide; 2-chloro-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropane-carboxamide; N-butyl-8-(1,1-dimethylethyl)-1-oxaspiro[4.5]decan-3-amine; sodium tetrathiocarbonate; as well as copper salts and preparations, such as Bordeaux mixture, copper hydroxide, copper naphthenate, copper oxychloride, copper sulfate, cufraneb, copper oxide, mancopper and oxine copper.

Bactericides:

Bronopol, dichlorophen; nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Akacaricides/Nematicides:

1. Acetylcholine Esterase (AChE) Inhibitors 1.1 Carbamates (such as alanycarb, aldicarb, aldoxycarb, allyxycarb, aminocarb, azamethiphos, bendiocarb, benfuracarb, bufencarb, butacarb, butocarboxim, butoxycarbonyl, carbaryl, carbofuran, carbosulfan, chloethocarb, coumaphos, cyanofenphos, cyanophos, dimetilan, ethiofencarb, fenobucarb, fenothiocarb, formetanate, furathiocarb, Isoprocarb, metals-sodium, methiocarb, methomyl, metolcarb, oxamyl, pirimicarb, promecarb, propoxur, thiodicarb, thiofanox, triazamate, trimethacarb, XMC and xylylcarb)

1.2 Organophosphates (such as acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl, -ethyl), coumaphos, cyanophos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl, -ethyl), phenthoate, phorate, phosalone, phosmet, phosphamidon, phosphocarb, phoxim, pirimiphos (-methyl, -ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Voltage-Dependent Sodium Channel Blockers 2.1 Pyrethroids (such as acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cyloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, trans-fluthrin, ZXI 8901, pyrethrins (pyrethrum)

2.2 Oxadiazines (such as indoxacarb)

3. Acetylcholine Receptor Agonists/Antagonists 3.1 Chloronicotinyls/neonicotinoides (such as acetamiprid, clothianidin, dinotefuran, imidacloprid, nitenpyram, nithiazine, thiacloprid, thiamethoxam)

3.2 Nicotine, bensultap, cartap

4. Acetylcholine Receptor Modulators 4.1 Spinosyns (such as spinosad)

5. GABA-Controlled Chloride Channel Antagonists 5.1 Cyclodiene organochlorine (such as camphechlor, chlordane, endosulfan, gamma-HCH, HCH, heptachlor, lindane, methoxychlor 5.2 Fiprols (such as acetoprole, ethiprole, fipronil, vaniliprole)

6. Chloride Channel Activators 6.1 Mectins (such as abamectin, avermectin, emamectin, emamectin-benzoate, ivermectin, milbemectin, milbemycin)

7. Juvenile Hormone Mimetics
(such as diofenolan, epofenonane, fenoxycarb, hydroprene, kinoprene, methoprene, pyriproxifen, triprene)

8. Ecdyson Agonists/Disruptors 8.1 Diacylhydrazine (such as chromafenozide, halofenozide, methoxyfenozide, tebufenozide)

9. Inhibitors of Chitin Biosynthesis 9.1 Benzoyl ureas (such as bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)

9.2 Buprofezin 9.3 Cyromazine

10. Inhibitors of Oxidative Phosphorylation, ATP Disruptors 10.1 Diafenthiuron 10.2 Organotins (such as azocyclotin, cyhexatin, fenbutatin oxides)

11. Uncoupler of Oxidative Phosphorylation by Interruption of the Proton Gradients
  11.1 Pyrroles (such as chlorfenapyr)
  11.2 Dinitrophenols (such as binapacryl, dinobuton, dinocap, DNOC)
12. Site I Electron Transport Inhibitors
  12.1 METIs (such as fenazaquin, fenpyroximate, pyrimidifen, pyridaben, tebufenpyrad, tolfenpyrad)
  12.2 Hydramethylnone
  12.3 Dicofol
13. Site Ii Electron Transport Inhibitors
  13.1 Rotenone
14. Site Iii Electron Transport Inhibitors
  14.1 Acequinocyl, fluacrypyrim
15. Microbial Disruptors of the Insect Intestinal Membrane Bacillus thuringiensis Strains
16. Fat Synthesis Inhibitors
  16.1 Tetronic acids (such as spirodiclofen, spiromesifen)
  16.2 Tetramic acids [such as 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No. 382608-10-8) and carbonic acid, cis-3-(2,5-dimethylphenyl)-8-methoxy-2-oxo-1-azaspiro[4.5]dec-3-en-4-yl ethyl ester (CAS Reg. No. 203313-25-1)]
17. Carboxamides
  (such as flonicamid)
18. Octopaminergic Agonists
  (such as amitraz)
19. Inhibitors of Magnesium-Stimulated ATPase
  (such as propargite)
20. Phthalamides
  (such as $N^2$-[1-dimethyl-2-(methylsulfonyl)ethyl]-3-iodo-N'-[2-methyl-4-[1,2,2,2-tetrafluoro-1-(trifluoromethyl)ethyl]phenyl]-1,2-benzenedicarboxamide (CAS Reg. No. 272451-65-7), flubendiamide)
21. Nereistoxin Analogs
  (such as thiocyclam hydrogen oxalate, thiosultap-sodium)
22. Bioorganisms, Hormones or Pheromones
  (such as azadirachtin, Bacillus spec., Beauveria spec., codlemone, Metarrhizium spec., Paecilomyces spec., thuringiensin, Verticillium spec.)
23. Active Substances with Unknown or Non-Specific Mechanisms of Action
  23.1 Gas treatment media (such as aluminium phosphide, methyl bromide, sulfuryl fluoride)
  23.2 Selective antifeedants (such as cryolite, flonicamid, pymetrozine)
  23.3 Mite growth inhibitors (such as clofentezine, etoxazole, hexythiazox)
  23.4 Amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin,
furthermore the compound 3-methyl-phenyl-propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo-isomers (CAS Reg. No. 185984-60-5) (see WO 96/37494, WO 98/25923), as well as preparations containing insecticidally effective plant extracts, nematodes, fungi or viruses.

Mixing with other known active substances, such as herbicides or with fertilizers and growth regulators, safeners or semiochemicals is also possible.

In addition, the inventive compounds of the formula (I) also show very good antimycotic activity. They have a very broad spectrum of antimycotic effectiveness, especially against dermatophytes and sprouting fungi, mold and diphasic fungi (for example against Candida species, such as Candida albicans, Candida glabrata) as well as Epidermophyton floccosum, Aspergillus species, such as Aspergillus niger and Aspergillus fumigatus, Trichophyton species, such as Trichophyton mentagrophytes, Microsporon species, such as Microsporon canis and audouinii. The listing of these fungi in no way represents a limitation of the ascertainable mycotic spectrum, but rather is only explanatory in character.

The active substances can be used as available, in formulations or application forms prepared therefrom, such as ready-to-use solutions, suspensions, spray powder, pastes, soluble powders, scattering agents and granulates. Application takes place in the usual manner, such as by pouring, spraying, showering, scattering, dusting, foam application, spreading, etc. Furthermore, it is possible to apply the active substances according to the ultra-low volume process or to inject the active substance itself into the ground. Seeds of the plants can also be treated.

For the use of the inventive active substances as fungicides, the application rates can be varied over a wide range, depending on the type of application. For treatment of plant parts, the application rates of active substance generally lie between 0.1 and 10,000 g/ha, preferably between and 1,000 g/ha. For treatment of seeds, the application rates of active substance generally lie between 0.001 and 50 g per kilogram of seed, preferably between 0.01 and 10 g per kilogram of seed. For soil treatment, the application rates of active substance generally lie between 0.1 and 10,000 g/ha, preferably between 1 and 5,000 g/ha.

As mentioned above, all plants and their parts can be treated in accordance with the invention. In a preferred embodiment, naturally occurring plant types and varieties and their parts can be treated, as well as those obtained by conventional biological cultivation methods, such as crossbreeding or protoplast fusion. In a further preferred embodiment, transgenic plants and plant types obtained by genetic technology methods, possibly in combination with conventional methods, (genetically modified organisms) and their parts are treated. The term "parts" or "parts of plants" or "plant parts" was explained above.

It is particularly preferred that plants typically available commercially in each case or plant types in use be treated in accordance with the invention. The term "plant types" is to be understood as plants with new characteristics ("traits") that have been produced by conventional cultivation, as well as those from mutagenesis or recombinant DNA techniques. These can be types, breeds, biotypes and genotypes.

Depending on the plant varieties or types, their location and growing conditions (soils, climates, vegetation cycle, nutrition), treatment in accordance with the invention can also show synergistic effects. Thus, for example, reduced application rates and/or increases in the spectrum of effectiveness and/or an intensification of the activity of the usable materials and agents according to the invention, improved plant growth, increased tolerance of high or low temperatures, increased tolerance of dryness or salt content of water or soil, increased flowering rates, easier harvesting, accelerated ripening, higher harvest yields, higher quality and/or higher nutritional value of the harvested products, improved storage characteristics and/or processability of the harvested products are possible, which go beyond the effects that are actually anticipated.

The category of transgenic plants or plant types (those obtained via genetic technology) to be treated preferentially according to the invention includes all plants that receive genetic material by modification using gene technology, said material giving these plants particularly advantageous, valuable characteristics ("traits"). Examples of such traits are improved plant growth, increased tolerance of high or low temperatures, increased tolerance of dryness or the salt content of water or soil, increased flowering rates, easier harvesting, accelerated ripening, higher harvest yields, higher quality and/or higher nutritional value of the harvested products, improved storage characteristics and/or processability of the harvested products. Other especially emphasized examples for such traits are an increase in the defenses of the plants against animal and microbial pests, such as against insects, mites, phytopathogenic fungi, bacteria and/or viruses as well as increased tolerance by the plants of particular herbicidal active substances. Examples of transgenic plants to mention are the important cultured plants, such as grains (wheat, rice), corn, soy, potatoes, cotton, tobacco and rape as well as fruit-bearing plants (with the fruits apples, pears, citrus and grapes), whereby corn, soy, potatoes, cotton, tobacco and rape are especially emphasized. Especially emphasized traits are increased resistance of plants to insects, cocooning pests, nematodes and snails as a result of toxins produced by the plants, especially those produced in the plants (referred to below as "Bt plants") by genetic material from *Bacillus thuringiensis* (such as by the genes CryIA(a), CryIA(b), CryIA (c), CryIIA, CryIIIA, CryIIIM2, Cry9c Cry2Ab, Cry3Bb and CryIF as well as their combinations). Especially emphasized traits also include increased resistance of plants to fungi, bacteria and viruses through systemic acquired resistance (SAR), systemin, phytoalexins and elicitors as well as resistance genes and corresponding expressed proteins and toxins. Additional especially emphasized traits are increased tolerance of the plants toward particular herbicidal active substances, such as imidazolinones, sulfonyl ureas, glyphosates or phosphinotricin (such as "PAT" genes). The genes providing the particular desired traits can also occur in combinations with one another in the transgenic plants. Examples of "Bt plants" are varieties of corn, cotton, soy and potato marketed under the trade names YIELD GARD® (for example corn, cotton, soy), KnockOut® (for example corn), StarLink® (for example corn), Bollgard® (cotton), Nucoton® (cotton) and NewLeaf® (potato). Examples of herbicide-tolerant plants are varieties of corn, cotton and soy marketed under the trade names Roundup Ready® (tolerance of glyphosates, for example corn, cotton, soy), Liberty Link® (tolerance of phosphinotricin, for example rape), IMI® (tolerance of imidazolinones) and STS® (tolerance of sulfonyl ureas, for example corn). Herbicide-resistant plants (conventionally cultured for herbicide-tolerance) plants are also the varieties marketed under the designation Clearfield® (for example corn). Of course these statements also apply to plant varieties developed or brought to market in the future with these genetic traits or ones developed in the future.

The plants listed can benefit especially from treatment with compounds of general formula (I) or active ingredient mixtures in accordance with the invention. The preferential areas cited above for the active substances or mixtures also apply to the treatment of these plants. Treatment of plants with the compounds or mixtures particularly listed in the present text is especially emphasized.

The synthesis and use of the active substances according to the invention can be seen in the following examples.

Synthesis Examples

Example 1

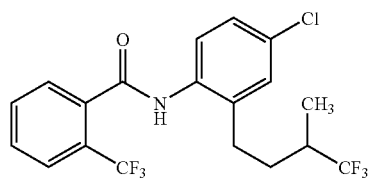

302.0 mg (1.2 mmol) 4-chloro-2-(4,4,4-trifluoroethyl-3-methyl-butyl)-phenylamine in 2 ml tetrahydrofuran are added to a solution consisting of 275.3 mg (1.3 mmol) 2-trifluoromethylbenzoyl chloride and 0.22 ml (1.6 mmol) triethylamine in 10 ml tetrahydrofuran. The reaction solution is stirred for 90 minutes at 60° C., filtered with silica gel and concentrated under vacuum.

505 mg of N-[4-chloro-2-(4,4,4-trifluoro-3-methylbutyl)-phenyl]-2-trifluoromethylbenzamide are obtained (99% theoretical yield) [log P (pH 2.3)=4.08].

Example 2

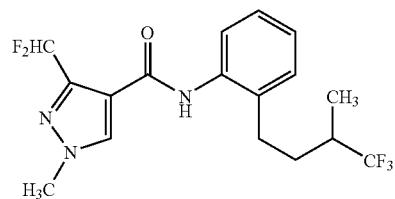

0.14 ml (1.7 mmol) oxalic acid dichloride and 4 drops of dimethyl formamide are added to a suspension of 264.2 mg (1.5 mmol) 3-difluoromethyl-1-methyl-1H-pyrazole-4-carboxylic acid in 9 ml dichloromethane. The reaction mixture is stirred for 2 hours at room temperature, then mixed with a solution of 325.9 mg (1.5 mmol) 2-(4,4,4-trifluoro-3-methylbutyl)-phenylamine and 0.29 ml (2.1 mmol) triethylamine in 9 ml dichloromethane. The reaction mixture is stirred at room temperature for 16 hours. The reaction is worked up by adding 7 ml of 2 N hydrochloric acid and stirring for 10 minutes at room temperature, then the organic phase is separated, dried over magnesium sulfate, filtered and concentrated under vacuum.

The yield is 525.0 mg of 3-difluoromethyl-1-methyl-1H-pyrazole-4-carboxyic acid, [2-(4,4,4-trifluoro-3-methylbutyl)-phenyl]-amide (89% theoretical yield) [log P (pH 2.3)=2.93].

The compounds of formula (I) listed below in Table 1 were obtained in an analogous manner to Examples 1 and 2, as well as according to the general description of the inventive synthesis processes (a) to (h).

TABLE 1
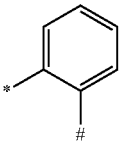
(I)
| No. | R | R¹ | R² | R³ | R⁴ | M | A | logP |
|---|---|---|---|---|---|---|---|---|
| 3 | H | CH₃ | C₂H₅ | Cl | H | 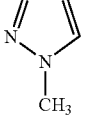 | 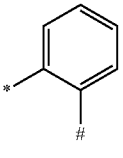 | 3.18 |
| 4 | H | CH₃ | C₂H₅ | Cl | H | 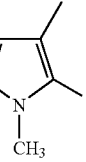 | 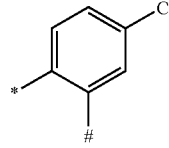 | 3.09 |
| 5 | H | H | CH₃ | CF₃ | H |  | 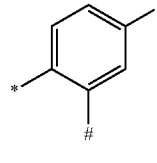 | 4.08 |
| 6 | H | H | CH₃ | CF₃ | H | 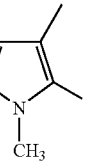 | 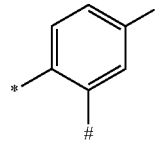 | 3.32 |
| 7 | H | H | CH₃ | CF₃ | H | 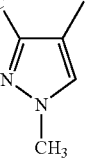 | 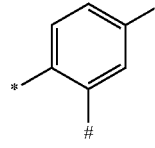 | 3.36 |
| 8 | H | H | CH₃ | CF₃ | H | 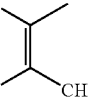 | 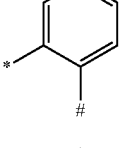 | 3.99 |
| 9 | H | H | CH₃ | CF₃ | H |  | 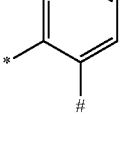 | 3.66 |
| 10 | H | H | CH₃ | CF₃ | H | 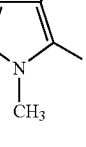 | | 2.84 |

TABLE 1-continued

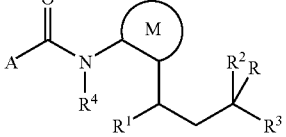

(I)

| No. | R | R¹ | R² | R³ | R⁴ | M | A | logP |
|---|---|---|---|---|---|---|---|---|
| 11 | H | H | $CH_3$ | $CF_3$ | H | 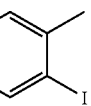 | 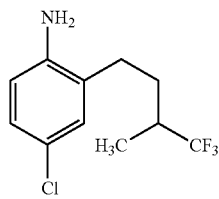 | 3.66 |

[a]) The bond marked with an asterisk ("*") is a link with the amide, and the bond marked with "#" is a link with the haloalkyl group.

Synthesis of Starting Materials of the Formula (III)

Example (III-1)

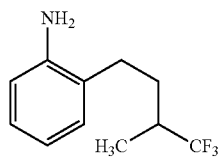

A solution of 7.0 g 1-(2-amino-5-chlorine-phenyl)-4,4,4-trifluoro-3-methylbutan-1-one (26 mmol), 4.0 g potassium hydroxide (60 mmol) and 3.0 g hydrazine hydrate (60 mmol) in 67 ml triethylene glycol is heated for 6 hours at 210° C. After cooling to room temperature, water and ethyl acetate are added, the phases are separated and the organic phase is washed again with water, dried over magnesium sulfate and the solvent is removed.

The yield is 4.9 g of 4-chloro-2-(4,4,4-trifluoro-3-methylbutyl)-phenylamine (73% theoretical yield).

$^1$H NMR (DMSO): δ=6.93 (m, 2H), 6.62 (d, 1H), 5.05 (s, 2H), 2.56 (m, 1H), 2.48-2.34 (m, 2H), 1.85 (m, 1H), 1.47 (m, 1H), 1.11 (d, 3H).

Example (III-2)

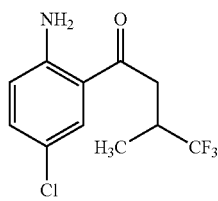

A solution of 2.3 g 4-chloro-2-(4,4,4-trifluoro-3-methylbutyl)-phenylamine (III-1) (9 mmol), 1.15 g ammonium formate (18 mmol) and 2.0 g Pd/C (5%, 0.9 mmol) in 21 ml methanol is stirred for an hour at room temperature. Afterward, the reaction solution is suction-filtered through Celite, washed with methanol and the filtrate is then rotovaped. Stirring the residue with pentane after removal of the solvent yields a solid that is suction-filtered and dried.

The yield is 1.7 g of 2-(4,4,4-trifluoro-3-methylbutyl)-phenylamine (86% theoretical yield).

$^1$H NMR (DMSO): δ=6.89 (m, 2H), 6.61 (m, 1H), 6.49 (m, 1H), 4.83 (s, 2H), 2.57 (m, 1H), 2.48-2.30 (m, 2H), 1.85 (m, 1H), 1.46 (m, 1H), 1.13 (d, 3H).

Synthesis of Starting Materials of the Formula (V)

Example (V-1)

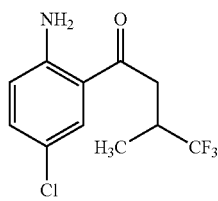

A solution of 10.0 g (29 mmol) N-[4-chloro-2-(4,4,4-trifluoro-3-methylbutyryl)-phenyl]-2,2-dimethylpropionamide in 366 ml 37% hydrochloric acid is refluxed for two days. After cooling to room temperature, the reaction is neutralized with 45% sodium hydroxide solution and the aqueous phase is extracted with dichloromethane. The organic phase is dried over sodium sulfate, and the yield after solvent removal is 7.1 g of 1-(2-amino-5-chlorophenyl)-4,4,4-trifluoro-3-methylbutane-1-one (93% theoretical yield).

$^1$H NMR (DMSO): δ=7.80 (d, 1H), 7.34 (s, 2H), 7.29 (dd, 1H), 6.82 (dd, 1H), 3.28 (dd, 1H), 3.14 (dd, 1H), 3.00 (m, 1H), 1.08 (d, 3H).

Synthesis of Starting Materials of the Formula (VI)

Example (VI-1)

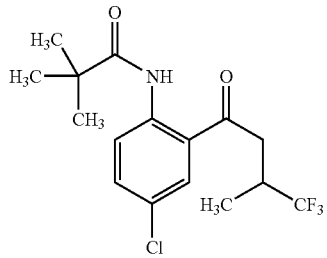

A solution of n-butyl lithium in hexane (1.6 M, 100 ml, 160 mmol) is added dropwise to a solution of 15.4 g N-(4-chlorophenyl)-2,2-dimethylpropionamide (73 mol) in 100 ml dry tetrahydrofuran at 0° C. and stirred for 2 hours at this temperature. Afterward, this solution is added dropwise at −70° C. to a solution of 13.4 g ethyl-(3-trifluoromethyl)-butyrate (73 mmol) in 250 ml dry tetrahydrofuran, and the reaction mixture is stirred at this temperature for one hour. After warming to room temperature, it is stirred for 16 hours. Hydrolysis with 100 ml water, concentration, dissolving the residue in dichloromethane/water and extracting the aqueous phase with dichloromethane, then drying the organic phase over sodium sulfate yields an educt/product mixture that can be separated by column chromatography on silica gel with 9:1 cyclohexane/ethyl acetate as the mobile phase.

The yield is 10.3 g of N-[4-chloro-2-(4,4,4-trifluoro-3-methylbutyryl)-phenyl]-2,2-dimethylpropionamide (40% theoretical yield).

$^1$H NMR (DMSO): δ=11.15 (s, 1H), 8.39 (d, 1H), 8.11 (d, 1H), 7.67 (dd, 1H), 3.47 (dd, 1H), 3.30 (dd, 1H), 2.99 (m, 1H), 1.25 (s, 9H), 1.15 (d, 3H).

The specified log P values are determined by HPLC on a reverse phase column (C18) in accordance with EEC Directive 79/831 Annex V.A8. Temperature: 43° C.

Eluents for the measurement in the acid range (pH 2.3): 0.1% aqueous phosphoric acid, acetonitrile; linearer gradient of 10% acetonitrile to 90% acetonitrile.

Calibration is performed with unbranched alkyl-2-ones (with 3 to 16 carbon atoms) with known log P values (determination of the log P values based on retention times by linear interpolation between two sequential alkyl ketones).

The lambda max. values were determined for the chromatographic signal peaks from the UV spectra in the 200 nm to 400 nm region.

Application Examples

Example A

*Sphaerotheca* Test (Cucumber)/Protective
Solvent:
24.5 parts by weight acetone
24.5 parts by weight dimethyl acetamide
Emulsifier: 1 part by weight alkyl aryl polyglycol ether To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, the plants are inoculated with an aqueous spore suspension of *Sphaerotheca fuliginea*. Then the plants are placed in the greenhouse at about 23° C. with relative humidity of about 70%.

The evaluation is performed seven days after the inoculation. A degree of effectiveness rating of 0% corresponds to the control, with 100% indicating no infestation observed.

TABLE A

Sphaerotheca test (cucumber)/protective

| Active substance according to the invention | Application rate of active substance in g/ha | Degree of effectiveness in % |
|---|---|---|
| (structure 1) | 100 | 95 |
| (structure 2) | 100 | 100 |
| (structure 3) | 100 | 100 |
| (structure 4) | 100 | 98 |

Example B

*Venturia* Test (Apple)/Protective
Solvent:
24.5 parts by weight acetone
24.5 parts by weight dimethyl acetamide
Emulsifier: 1 part by weight alkyl aryl polyglycol ether To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, the plants are inoculated with an aqueous conidia suspension of the apple scab pathogen *Venturia inaequalis* and are then kept in an incubator at 20° C. and 100% relatively humidity for one day.

Then the plants are placed in the greenhouse at about 21° C. with relative humidity of about 90%.

The evaluation is performed ten days after the inoculation. A degree of effectiveness rating of 0% corresponds to the control, with 100% indicating no infestation observed.

TABLE B

| Venturia test (apple)/protective | | |
|---|---|---|
| Active substance according to the invention | Application rate of active substance in g/ha | Degree of effectiveness in % |
| 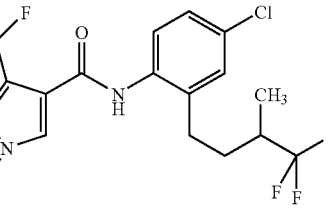 | 100 | 93 |
| 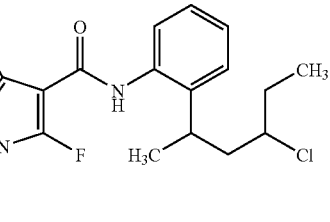 | 100 | 100 |
| 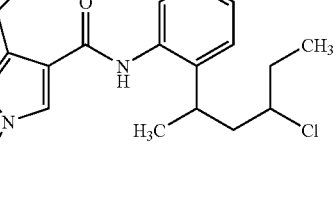 | 100 | 100 |
| 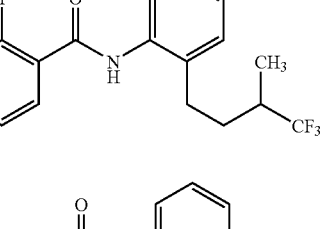 | 100 | 94 |
| 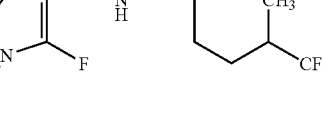 | 100 | 94 |

TABLE B-continued

| Venturia test (apple)/protective | | |
|---|---|---|
| Active substance according to the invention | Application rate of active substance in g/ha | Degree of effectiveness in % |
| 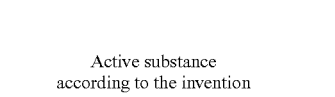 | 100 | 97 |

Example C

*Botrytis* Test (Bean)/Protective

Solvent:
24.5 parts by weight acetone
24.5 parts by weight dimethyl acetamide

Emulsifier: 1 part by weight alkyl aryl polyglycol ether

To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, two small pieces of agar with cultured *Botrytis cinerea* are placed on each leaf. The inoculated plants are placed in a darkened chamber at about 20° C. and 100% relatively humidity.

Two days after the inoculation, the size of the infestation spots on the leaves is evaluated. A degree of effectiveness rating of 0% corresponds to the control, with 100% indicating no infestation observed.

TABLE C

| Botrytis test (bean)/protective | | |
|---|---|---|
| Active substance according to the invention | Application rate of active substance in g/ha | Degree of effectiveness in % |
| 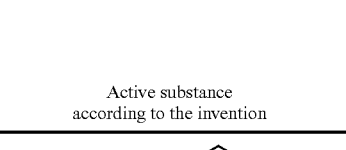 | 500 | 82 |
| 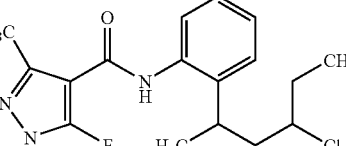 | 500 | 100 |

TABLE C-continued

Botrytis test (bean)/protective

| Active substance according to the invention | Application rate of active substance in g/ha | Degree of effectiveness in % |
|---|---|---|
| 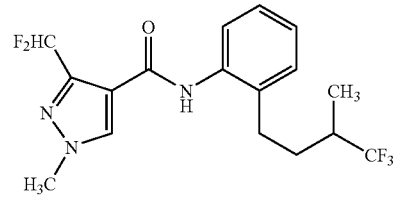 | 500 | 99 |

Example D

*Puccinia* Test (Wheat)/Protective
Solvent: 50 parts by weight N,N-dimethyl acetamide
Emulsifier: 1 part by weight alkyl aryl polyglycol ether To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, the plants are sprayed with a conidia suspension of *Puccinia recondita*. The plants are kept in an incubator at 20° C. and 100% relatively humidity for 48 hours.

Then the plants are placed in a greenhouse at a temperature of about 20° C. and a relatively humidity of 80%, in order to promote the development of rust spots.

The evaluation is performed ten days after the inoculation. A degree of effectiveness rating of 0% corresponds to the control, with 100% indicating no infestation observed.

TABLE D

Puccinia test (wheat)/protective

| Active substance according to the invention | Application rate of active substance in g/ha | Degree of effectiveness in % |
|---|---|---|
| 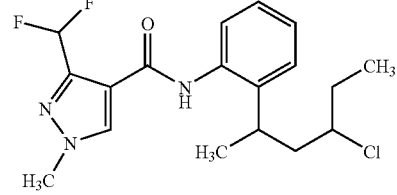 | 500 | 100 |
|  | 500 | 100 |

TABLE D-continued

Puccinia test (wheat)/protective

| Active substance according to the invention | Application rate of active substance in g/ha | Degree of effectiveness in % |
|---|---|---|
| 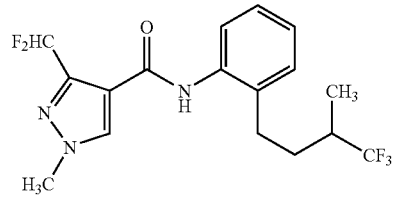 | 500 | 100 |

Example E

*Alternaria* Test (Tomato)/Protective
Solvent: 49 parts by weight N,N-dimethyl formamide
Emulsifier: 1 part by weight alkyl aryl polyglycol ether To produce an appropriate active ingredient preparation, one part by weight of the active substance is mixed with the specified quantities of solvent and emulsifying agent, and the concentrate is diluted with water to the desired concentration.

Young tomato plants are sprayed with the active ingredient preparation at the specified application rate to test the effectiveness of protection. One day after treatment, the plants are inoculated with a spore suspension of *Alternaria solani* and are kept for 24 hours at 100% relatively humidity and 20° C. Subsequently, the plants are kept at 96% relatively humidity and a temperature of 20° C.

The evaluation is performed seven days after the inoculation. A degree of effectiveness rating of 0% corresponds to the control, with 100% indicating no infestation observed.

TABLE E

Alternaria test (tomato)/protective

| Active substance according to the invention | Application rate of active substance in g/ha | Degree of effectiveness in % |
|---|---|---|
| 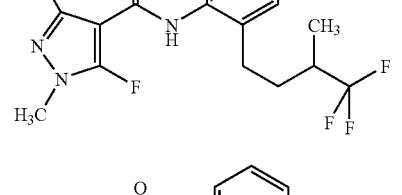 | 750 | 90 |
| 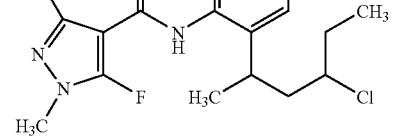 | 750 | 100 |

TABLE E-continued

Alternaria test (tomato)/protective

| Active substance according to the invention | Application rate of active substance in g/ha | Degree of effectiveness in % |
|---|---|---|
| 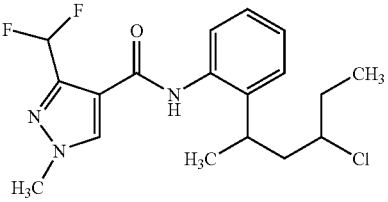 | 750 | 95 |

The invention claimed is:

1. A haloalkyl carboxamide of the formula (I)

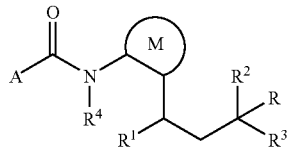

(I)

in which

R stands for hydrogen or halogen, $R^1$ stands for hydrogen or methyl, $R^2$ stands for methyl, ethyl or $C_1$-$C_4$ haloalkyl with 1 to 9 fluorine, chlorine and/or bromine atoms, $R^3$ stands for halogen or $C_1$-$C_4$ haloalkyl with 1 to 9 fluorine, chlorine and/or bromine atoms, $R^4$ stands for hydrogen, $C_1$-$C_8$ alkyl, $C_1$-$C_6$ alkylsulfinyl, $C_1$-$C_6$ alkylsulfonyl, $C_1$-$C_4$-alkoxy-$C_1$-$C_4$-alkyl, $C_3$-$C_8$ cycloalkyl; $C_1$-$C_6$ haloalkyl, $C_1$-$C_4$ haloalkylthio, $C_1$-$C_4$ haloalkylsulfinyl, $C_1$-$C_4$ haloalkylsulfonyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$ alkyl)carbonyl-$C_1$-$C_3$-alkyl, ($C_1$-$C_3$ alkoxy)carbonyl-$C_1$-$C_3$-alkyl; halo-($C_1$-$C_3$ alkyl)carbonyl-$C_1$-$C_3$-alkyl, halo-($C_1$-$C_3$ alkoxy)carbonyl-$C_1$-$C_3$-alkyl with 1 to 13 fluorine, chlorine and/or bromine atoms in each case; ($C_1$-$C_8$ alkyl)carbonyl, ($C_1$-$C_8$ alkoxy)carbonyl, ($C_1$-$C_4$-alkoxy-$C_1$-$C_4$-alkyl)carbonyl, ($C_3$-$C_8$ cycloalkyl)carbonyl; ($C_1$-$C_6$ haloalkyl)carbonyl, ($C_1$-$C_6$ haloalkoxy)carbonyl, (halo-$C_1$-$C_4$-alkoxy-$C_1$-$C_4$-alkyl)carbonyl, ($C_3$-$C_8$ halocycloalkyl)carbonyl with 1 to 9 fluorine, chlorine and/or bromine atoms in each case; or —C(=O)C(=O)$R^5$, —CONR$^6$R$^7$ or —CH$_2$NR$^8$R$^9$, $R^5$ stands for hydrogen, $C_1$-$C_8$ alkyl, $C_1$-$C_8$ alkoxy, $C_1$-$C_4$-alkoxy-$C_1$-$C_4$-alkyl, $C_3$-$C_8$ cycloalkyl; $C_1$-$C_6$ haloalkyl, $C_1$-$C_6$ haloalkoxy, halo-$C_1$-$C_4$-alkoxyl-$C_1$-$C_4$-alkyl, $C_3$-$C_8$ halocycloalkyl with 1 to 9 fluorine, chlorine and/or bromine atoms in each case, $R^6$ and $R^7$ stand independently of one another in each case for hydrogen, $C_1$-$C_8$ alkyl, $C_1$-$C_4$ alkoxyl $C_1$-$C_4$ allyl, $C_3$-$C_8$ cycloalkyl; $C_1$-$C_8$ haloalkyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case, or $R^6$ and $R^7$, together with the nitrogen atom to which they are bound, form a substituted, saturated heterocycle with 5 to 8 ring atoms, with single or multiple, the same or different substitution by halogen or $C_1$-$C_4$ alkyl, whereby the heterocycle optionally contains 1 or 2 additional, non-adjacent hetero atoms constituted of oxygen, sulfur or NR$^{10}$, $R^8$ and $R^9$ stand independently of one another for hydrogen, $C_1$-$C_8$-alkyl, $C_3$-$C_8$ cycloalkyl; $C_1$-$C_8$ haloalkyl, $C_3$-$C_8$ halocycloalkyl with 1 to 9 fluorine, chlorine and/or bromine atoms in each case, or $R^8$ and $R^9$, together with the nitrogen atom to which they are bound, form a substituted, saturated heterocycle with 5 to 8 ring atoms, with single or multiple, the same or different substitution by halogen or $C_1$-$C_4$ alkyl, whereby the heterocycle optionally contains 1 or 2 additional, non-adjacent hetero atoms constituted of oxygen, sulfur or NR$^{10}$, $R^{10}$ stands for hydrogen or $C_1$-$C_6$ alkyl, M stands in each case for a phenyl ring with a single substitution by $R^{11}$, $R^{11}$ stands for hydrogen, fluorine, chlorine, methyl, isopropyl, methylthio or trifluoromethyl, A stands for the group of the formula (A1)

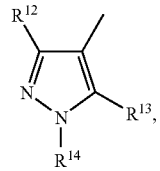

(A1)

in which $R^{12}$ stands for hydrogen, cyano, halogen, nitro, $C_1$-$C_4$ alkyl, $C_1$-$C_4$ alkoxy, $C_1$-$C_4$ alkylthio, $C_3$-$C_6$ cycloalkyl, haloalkyl, $C_1$-$C_4$ haloalkoxy or $C_1$-$C_4$ haloalkylthio, in each case with 1 to 5 halogen atoms, aminocarbonyl or aminocarbonyl-$C_1$-$C_4$-alkyl, $R^{13}$ stands for hydrogen, halogen, cyano, $C_1$-$C_4$ alkyl, $C_1$-$C_4$ alkoxy or $C_1$-$C_4$ alkylthio, and $R^{14}$ stands for hydrogen, $C_1$-$C_4$ alkyl, hydroxy-$C_1$-$C_4$ alkyl, $C_2$-$C_6$ alkenyl, $C_3$-$C_6$ cycloalkyl, $C_1$-$C_4$-alkylthio-$C_1$-$C_4$-alkyl, $C_1$-$C_4$-alkoxy-$C_1$-$C_4$-alkyl, $C_1$-$C_4$ haloalkyl, $C_1$-$C_4$-haloalkylthio-$C_1$-$C_4$-alkyl, $C_1$-$C_4$-haloalkoxy-$C_1$-$C_4$-alkyl in each case with 1 to 5 halogen atoms, or phenyl.

2. A haloalkyl carboxamide of the formula (I) according to claim 1, in which

R stands for hydrogen, fluorine, chlorine or bromine, $R^1$ stands for hydrogen or methyl, $R^2$ stands for methyl, ethyl or in each case for methyl, ethyl, n- or isopropyl, n-, iso-, sec- or tert-butyl with single or multiple, the same or different, substitution by fluorine, chlorine or bromine, $R^3$ stands for fluorine, chlorine, bromine, iodine or in each case for methyl, ethyl, n- or isopropyl, n-, iso-, sec- or tert-butyl with single or multiple, the same or different, substitution by fluorine, chlorine or bromine, $R^4$ stands for hydrogen, $C_1$-$C_4$ alkyl, $C_1$-$C_4$ alkylsulfinyl, $C_1$-$C_4$ alkylsulfonyl, $C_1$-$C_4$-alkoxy-$C_1$-$C_4$-alkyl, $C_3$-$C_6$ cycloalkyl; $C_1$-$C_4$ haloalkyl, $C_1$-$C_4$ haloalkylthio, $C_1$-$C_4$ haloalkylsulfinyl, $C_1$-$C_4$ haloalkylsulfonyl, halo-$C_1$-$C_3$-alkoxy-$C_1$-$C_3$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$ alkyl)carbonyl-$C_1$-$C_3$-alkyl, ($C_1$-$C_3$ alkoxy)carbonyl-$C_1$-$C_3$-alkyl; halo- ($C_1$-$C_3$ alkyl)carbonyl-$C_1$-$C_3$-alkyl, halo-($C_1$-$C_3$ alkoxy)carbonyl-$C_1$-$C_3$-alkyl with 1 to 13 fluorine, chlorine and/or bromine atoms in each case; ($C_1$-$C_6$ alkyl)carbonyl, ($C_1$-$C_4$ alkoxy)carbonyl, ($C_1$-$C_3$-alkoxy-$C_1$-$C_3$ alkyl)carbonyl, ($C_3$-$C_6$ cycloalkyl)carbonyl; ($C_1$-$C_4$ haloalkyl)carbonyl, ($C_1$-$C_4$ haloalkoxy)carbonyl, (halo-$C_1$-$C_3$-alkoxy-$C_1$-$C_3$-alkyl)carbonyl, ($C_3$-$C_6$ halocycloalkyl)carbonyl with 1 to 9 fluorine, chlorine and/or bromine atoms in each case; or —C(=O)C(=O)$R^5$, —CONR$^6$R$^7$ or —CH$_2$NR$^8$R$^9$, $R^5$ stands for hydrogen, $C_1$-$C_6$ alkyl, $C_1$-$C_4$ alkoxy, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkoxy, halo-$C_1$-$C_3$-alkoxy-$C_1$-$C_3$-alkyl, $C_3$-$C_6$ halocycloalkyl with 1 to 9 fluorine, chlorine and/or bromine atoms in each case, $R^6$ and $R^7$ stand independently of one another in each case for hydrogen, $C_1$-$C_6$ alkyl, $C_1$-$C_3$-alkoxy-$C_1$-$C_3$-alkyl, $C_3$-$C_6$ cycloalkyl; $C_1$-$C_4$ haloalkyl, halo-$C_1$-$C_3$-alkoxy-$C_1$-$C_3$-alkyl, $C_3$-$C_6$ halocycloalkyl with 1 to 9 fluorine, chlorine and/or bromine atoms in each case, or $R^6$ and $R^7$, together with the nitrogen atom to which they are bound, form a substituted, saturated heterocycle with 5 to 8 ring atoms, with single or multiple, the same or different substitution by halogen or $C_1$-$C_4$ alkyl, whereby the heterocycle optionally contains 1 or 2 additional, non-adjacent hetero atoms constituted of oxygen, sulfur or NR$^{10}$, $R^8$ and $R^9$ stand independently of one another for hydrogen, $C_1$-$C_6$ alkyl, $C_3$-$C_6$ cycloalkyl; —$C_4$ haloalkyl, $C_3$-$C_6$ halocycloalkyl with 1 to 9 fluorine, chlorine and/or bromine atoms in each case, or $R^8$ and $R^9$, together with the nitrogen atom to which they are bound, form a substituted, saturated heterocycle with 5 to 8 ring atoms, with single or multiple, the same or different substitution by halogen or $C_1$-$C_4$ alkyl, whereby the heterocycle optionally contains 1 or 2 additional, non-adjacent hetero atoms constituted of oxygen, sulfur or NR$^{10}$, $R^{10}$ stands for hydrogen or $C_1$-$C_4$ alkyl, M stands for the following cyclic

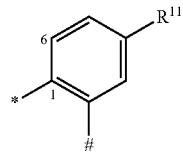

(M-1)

whereby the bond marked with an asterisk ("*") is a link with the amide, and the bond marked with "#" is a link with the haloalkyl group, $R^{11}$ stands for hydrogen, fluorine, chlorine, methyl or trifluoromethyl, A stands for the group of the formula (A1)

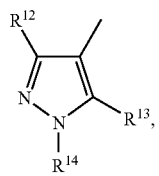

(A1)

in which $R^{12}$ stands for hydrogen, cyano, fluorine, chlorine, bromine, iodine, methyl, ethyl, isopropyl, methoxy, ethoxy, methylthio, ethylthio, cyclopropyl, $C_1$-$C_2$ haloalkyl, $C_1$-$C_2$ haloalkoxy in each case with 1 to 5 fluorine, chlorine and/or bromine atoms, trifluoromethylthio, difluoromethylthio, aminocarbonyl, aminocarbonylmethyl or aminocarbonylethyl, $R^{13}$ stands for hydrogen, fluorine, chlorine, bromine, iodine, methyl, ethyl, methoxy, ethoxy, methylthio or ethylthio, and $R^{14}$ stands for hydrogen, methyl, ethyl, n-propyl, isopropyl, $C_1$-$C_2$ haloalkyl with 1 to 5 fluorine, chlorine and/or bromine atoms, hydroxymethyl, hydroxyethyl, cyclopropyl, cyclopentyl, cyclohexyl or phenyl.

3. A process for synthesizing a haloalkyl carboxamide of the formula (I) according to claim 1, comprising a) reacting a carboxylic acid derivative of the formula (II)

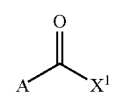

(II)

in which

A has the meaning as defined above in claim 1 and $X^1$ stands for halogen or hydroxy, with an aniline derivative of the formula (III)

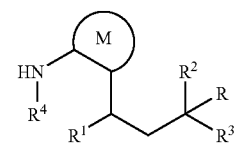

(III)

in which

R, $R^1$, $R^2$, $R^3$, $R^4$ and M have the meanings as defined above in claim 1, optionally in the presence of a catalyst, optionally in the presence of a condensation agent, optionally in the presence of an acid binder and optionally in the presence of a diluent, or b) reacting a haloalkylcarboxanilide of the formula (I-a)

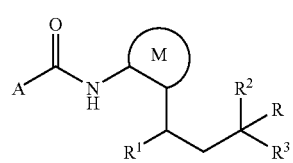

(I-a)

in which

R, $R^1$, $R^2$, $R^3$, M and A have the meanings as defined above in claim 1, with a halide of the formula (IV)

$$R^{4-A}—X^2 \qquad (IV)$$

in which $X^2$ stands for chlorine, bromine or iodine, $R^{4-A}$ stands for $C_1$-$C_8$ alkyl, $C_1$-$C_6$ alkylsulfinyl, $C_1$-$C_6$ alkylsulfonyl, $C_1$-$C_4$ alkoxy-$C_1$-$C_4$ alkyl, $C_3$-$C_8$ cycloalkyl; $C_1$-$C_6$ haloalkyl, haloalkylthio, $C_1$-$C_4$ haloalkylsulfinyl, $C_1$-$C_4$ haloalkylsulfonyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$ alkyl)carbonyl-$C_1$-$C_3$-alkyl, ($C_1$-$C_3$ alkoxy)carbonyl-$C_1$-$C_3$-alkyl; halo-($C_1$-$C_3$ alkyl)carbonyl-$C_1$-$C_3$-alkyl, halo-($C_1$-$C_3$ alkoxy)carbonyl-$C_1$-$C_3$-alkyl with 1 to 13 fluorine, chlorine and/or bromine atoms in each case; ($C_1$-$C_8$ alkyl)carbonyl, ($C_1$-$C_8$ alkoxy)carbonyl, ($C_1$-$C_4$-alkoxy-$C_1$-$C_4$-alkyl)carbonyl, ($C_3$-$C_8$ cycloalkyl)carbonyl; ($C_1$-$C_6$ haloalkyl)carbonyl, ($C_1$-$C_6$ haloalkoxy)carbonyl, (halo-$C_1$-$C_4$-alkoxy-$C_1$-$C_4$-alkyl)carbonyl, ($C_3$-$C_8$ halocycloalkyl)carbonyl with 1 to 9 fluorine, chlorine and/or bromine atoms in each case; or —C(=O)C(=O)$R^5$, —CONR$^6$R$^7$ or —CH$_2$NR$^8$R$^9$, whereby $R^5$, $R^6$, $R^7$, $R^8$ and $R^9$ have the meanings as defined above in claim 1, in the presence of a base and a dilution medium.

4. A composition for combating undesirable microorganisms, comprising at least one haloalkyl carboxamide of the formula (I) according to claim 1 together with extenders and/or surface-active materials.

5. A method for combating undesired microorganisms, comprising applying at least one haloalkyl carboxamide of the formula (I) according to claim 1 to the microorganisms and/or their environment.

6. A method for preparing a composition to combat undesired microorganisms, comprising mixing at least one haloalkyl carboxamide of the formula (I) according to claim 1 with extenders and/or surface-active materials.

\* \* \* \* \*